(12) United States Patent
Okamoto et al.

(10) Patent No.: US 9,790,155 B2
(45) Date of Patent: Oct. 17, 2017

(54) POLYETHER DIOL AND METHOD FOR PRODUCING THE SAME

(71) Applicant: Mitsubishi Gas Chemical Company, Inc., Tokyo (JP)

(72) Inventors: Atsushi Okamoto, Niigata (JP); Hideyuki Sato, Niigata (JP); Yoshiaki Yamamoto, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 14/758,084

(22) PCT Filed: Dec. 27, 2013

(86) PCT No.: PCT/JP2013/085211
§ 371 (c)(1),
(2) Date: Jun. 26, 2015

(87) PCT Pub. No.: WO2014/104341
PCT Pub. Date: Jul. 3, 2014

(65) Prior Publication Data
US 2015/0329454 A1    Nov. 19, 2015

(30) Foreign Application Priority Data
Dec. 28, 2012  (JP) .................. 2012-287275

(51) Int. Cl.
*C07C 41/28* (2006.01)
*C07C 43/13* (2006.01)

(52) U.S. Cl.
CPC ............ *C07C 41/28* (2013.01); *C07C 43/132* (2013.01); *C07C 43/135* (2013.01)

(58) Field of Classification Search
None
See application file for complete search history.

(56) References Cited

U.S. PATENT DOCUMENTS

| | | |
|---|---|---|
| 3,287,419 A | 11/1966 | Duke et al. |
| 5,780,687 A | 7/1998 | Holderich et al. |
| 5,821,391 A | 10/1998 | Holderich et al. |
| 5,877,255 A | 3/1999 | Gerber et al. |
| 6,657,089 B1 | 12/2003 | Nagasawa et al. |

| | | | |
|---|---|---|---|
| 2002/0157578 A1 | 10/2002 | Wombacher et al. | |
| 2008/0188354 A1 | 8/2008 | Pauws et al. | |
| 2011/0216123 A1 | 9/2011 | Tamai et al. | |

FOREIGN PATENT DOCUMENTS

| | | | | |
|---|---|---|---|---|
| JP | H7-25804 A | 1/1995 | | |
| JP | H7-82193 A | 3/1995 | | |
| JP | H07224290 A | * 8/1995 | .......... | C10M 105/48 |
| JP | 10-7622 A | 1/1998 | | |
| JP | H10-67698 A | 3/1998 | | |
| JP | 2977782 B2 | 9/1999 | | |
| JP | 2000-219557 A | 8/2000 | | |
| JP | 2004-18464 A | 1/2004 | | |
| JP | 2004-514014 A | 5/2004 | | |
| JP | 2008-19260 A | 1/2008 | | |
| JP | 2012-21132 A | 2/2012 | | |
| WO | 02/38688 A2 | 5/2002 | | |

OTHER PUBLICATIONS

International Search Report date of mailing Apr. 8, 2014 for PCT/JP2013/085211 and English translation of the same.
"No495—Sur la deshydratation acide du dimethyl 1-2,2 propanediol-1,3 et de quelques autres propanediols-1,3 disubstitues en 2. 1.—Deshydration acide du dimethyl-2,2 propanediol-1,3."; Bulletin de la Societe Chimique de France(1967), (8), 2755-2763; Teophile Yvernault and Michel Mazet; Mar. 14, 1967 (No English translation available).
"Cyclic Trimerization of Oxetanes"; 9 Acta Chemica Scandinavica vol. 45(1) p. 82-91(1991); Johannes Dale and Siw B. Fredriksen.
"Thermotropic Liquid Crystal Polyesters Derived From 4, 4'-Biphenyldicarbozylic Acid and Oxyalkylene Spacers"; Macromolecular Symposia, 1994, 84, 297-306; Antonio Bello, Jose Manuel Prena, Ernesto Prez and Rosario Benavente.

* cited by examiner

*Primary Examiner* — Rosalynd Keys
(74) *Attorney, Agent, or Firm* — Fitch, Even, Tabin & Flannery, LLP

(57) ABSTRACT

A method for producing a polyether diol includes the step of subjecting a compound represented by the following general formula (1) to hydrogenation reduction in the presence of a hydrogenation catalyst to provide a specific polyether diol.

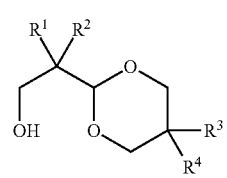

(1)

18 Claims, 11 Drawing Sheets

POLYETHER DIOL AND METHOD FOR PRODUCING THE SAME

CROSS-REFERENCE TO RELATED APPLICATIONS

This application is a U.S. national phase application filed under 35 U.S.C. §371 of International Application PCT/JP2013/085211, filed on Dec. 27, 2013, designating the United States, which claims priority from Japanese Application Number 2012-287275, filed on Dec. 28, 2012, which are hereby incorporated herein by reference in their entirety.

TECHNICAL FIELD

The present invention relates to a polyether diol and a method for producing the same.

BACKGROUND ART

A polyether diol is a compound which is widely utilized for various applications. The polyether diol is generally a compound having a hydroxyl group at each of both terminals of an oxyalkylene chain. The compound is obtained by polymerizing ethylene oxide or propylene oxide. 2,2-Dialkyl-1,3-propanediol to which ethylene oxide or propylene oxide is added is also known as a modified polyether diol. As an example of the applications of the modified polyether diol, Japanese Patent Application Laid-Open No. 2008-19260 discloses an agrochemical composition; Japanese Patent Application Laid-Open No. 2000-219557 discloses a concrete additive composition; and Japanese Patent Application Laid-Open No. 10-7622 discloses a resin composition or the like.

Conventionally, a method for subjecting 2,2-disubstituted-1,3-propanediol to ring-opening addition of ethylene oxide or propylene oxide is well known as a method for producing a modified polyether diol having a 2,2-disubstituted-1,3-propanediol skeleton (hereinafter, referred to as a "neo skeleton"). While on the other hand, examples disclosing a method for producing a polyether diol including only a neo skeleton are scarce. One of the examples is disclosed in Bulletin de la Societe Chimiquede France (1967), (8), 2755-2763. A method for obtaining di-neopentyl glycol from neopentyl glycol is disclosed as a method for producing a polyether diol by an intermolecular dehydration reaction using an acid catalyst in Bulletin de la Societe Chimiquede France (1967), (8), 2755-2763. A method for producing another polyether diol having a neo skeleton is disclosed in Acta Chemica Scandinavica vol. 45 (1) p 82-91 (1991). A method for simultaneously obtaining di-neopentyl glycol and tri-neopentyl glycol from 3,3-dimethyl oxetane is disclosed as a method for producing a polyether diol by a polymerization reaction of an oxetane compound in Acta Chemica Scandinavica vol. 45 (1) p 82-91 (1991). Furthermore, a method for producing other polyether diol having a neo skeleton is disclosed in U.S. Pat. No. 3,287,419. A method for obtaining 3,3'-oxybis-(2,2-dimethyl-1-propanol) (hereinafter, sometimes referred to as di-neopentyl glycol) from 2,2-dimethyl-3-hydroxy-propionaldehyde and 3,3'-oxybis-(2-ethyl-2-butyl-1-propanol) from 2-ethyl-2-butyl-3-hydroxy-propionaldehyde is disclosed as a method for polymerizing 2,2-dialkyl-3-hydroxy-propionaldehyde using an acid catalyst to provide a polymer, and thereafter reducing the polymer to produce a polyether diol in U.S. Pat. No. 3,287,419.

In the meantime, a reaction for reductively ring-opening a cyclic acetal compound having a 1,3-dioxane structure using a hydrogenation catalyst is known as a method for producing an ether compound containing a hydroxyl group. Specifically, the following producing method is disclosed. That is, a method for hydrogenating a substituted 1,3-dioxane compound using a catalyst containing a Group IB metal in the Periodic Table and an acid carrier to produce a 3-alkoxy-propane-1-ol compound is disclosed in Japanese Patent No. 2977782.

SUMMARY OF INVENTION

In the method described in Bulletin de la Societe Chimiquede France (1967), (8), 2755-2763, a reaction is performed in a high temperature region of 180 to 190° C. by using a strongly acidic catalyst. Therefore, the method cannot avoid the decomposition and sequential side reaction of the polyether diol, which disadvantageously causes a decrease in a reaction selectivity. In the method described in Acta Chemica Scandinavica vol. 45 (1) p 82-91 (1991), the oxetane compound as the raw material is expensive. Furthermore, the oxetane compound has high reactivity, and very easily causes a secondary reaction, which disadvantageously causes a decrease in the reaction selectivity of the polyether diol. In the method described in U.S. Pat. No. 3,287,419, the structure of the polymer intermediately produced is a complicated skeleton structure. It is difficult to reduce the polymer to obtain the polyether diol at a good reaction selectivity. A specific yield is not described in the document.

A general formula as the substituted 1,3-dioxane compound used as the raw material for hydrogenation reduction is shown in Japanese Patent No. 2977782. However, only an example of 5,5-dimethyl-2-phenyl-1,3-dioxane is described in Examples. Generation of the polyether diol and simultaneous generation of a higher polyether diol are not disclosed and suggested at all. Although an example of a polyether diol including a single neo skeleton is disclosed in these conventionally known documents, a polyether diol including at least two neo skeletons is not referred to.

The modified polyether diol contained in the composition described in Japanese Patent Application Laid-Open Nos. 2008-19260, 2000-219557 and 10-7622 has different units, i.e., a neo skeleton and an ethylene glycol or propylene glycol skeleton in a molecule. The neo skeleton has excellent chemical stability such as weatherability or oxidation resistance provided by a quaternary carbon structure, whereas the ethylene glycol or propylene glycol skeleton tends to be poor in these properties. Therefore, for example, National Publication of International Patent Application No. 2004-514014 points out that an alkoxy site derived from the ethylene glycol or propylene glycol skeleton is oxidized with time and deteriorated, and whereby predetermined performance cannot be exhibited when a main chain of a polymer is formed by using a propoxylated neopentyl glycol derivative, in paragraphs 0050 to 0052. In order to avoid the problem caused by the chemical instability of the alkoxy site, a polyether diol including only a neo skeleton is desired.

Furthermore, a polyol having a neo skeleton that is typified by neopentyl glycol, i.e., 2,2-dimethyl-1,3-propanediol, and its derivative generally have a melting point higher than room temperature. The melting point of neopentyl glycol is 125 C. If neopentyl glycol is not melted before the use when being stored in a solid state, a sufficient mixed state is less likely to be obtained when neopentyl glycol is mixed with other substances. In order to avoid the insufficient mixed state, a method for transporting and storing neopentyl glycol at a temperature of 130 to 150 C is also employed. However, there is known that the high temperature disadvantageously causes deterioration with time. Then, for example, a treatment described in Japanese Patent Application Laid-Open No. 07-82193 is required.

In the meantime, a chemical substance generally tends to have a lower melting point and boiling point as it has an asymmetric structure (poor symmetry) (rule of Carnelley). Di-neopentyl glycol which is a polyether diol obtained by dehydrogenation of two molecules of neopentyl glycol (melting point: 125° C.) has an ether bond in a molecule, and thereby the melting point of di-neopentyl glycol is decreased to 85° C. Furthermore, the melting point of tri-neopentyl glycol having an increased ether bond is decreased to 69° C. Even if two substituent groups bonded to a carbon atom (quaternary carbon) at 2-position of 2,2-disubstituted-1,3-propanediol are substituted with substituent groups different from each other, the same effect is recognized. For example, the melting point of 2-methyl-2-propyl-1,3-propanediol is 57° C. Accordingly, the asymmetry of the polyol compound including only the neo skeleton is increased, and thereby the melting point is further decreased, which can be considered to avoid or reduce the above-mentioned disadvantage, to provide simpler utilization.

Examples of more asymmetric structures of the polyether diol, only comprising neo skeletons with one or more ether bonds in a molecule, include one that has at least two kinds of neo skeletons, or one that has at least one quaternary carbon (2-position carbon) which is bonding with two different substituent groups. A method for efficiently producing the polyether diol is desired.

In order to solve the above problems in the conventional technique, it is an object of the present invention to provide a method for efficiently producing a polyether diol. It is another object of the present invention to provide a novel polyether diol obtained by using the producing method.

The present inventors have made eager research on a method for efficiently producing a polyether diol. As a result, the present inventors have found a method for hydrogenating a specific cyclic acetal compound in the presence of a hydrogenation catalyst to efficiently produce polyether diols and their mixtures. The present invention is based on this finding.

That is, the present invention is as follows.

[1] A method for producing a polyether diol, comprising subjecting a compound represented by the following general formula (1) to hydrogenation reduction in the presence of a hydrogenation catalyst to provide at least one polyether diol selected from the group consisting of compounds represented by the following general formulae (2), (3A), (3B), (3C), and (3D):

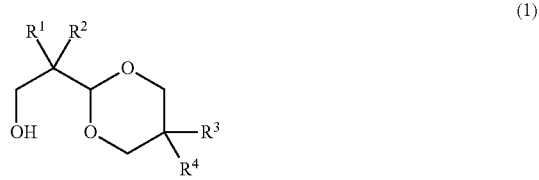

(1)

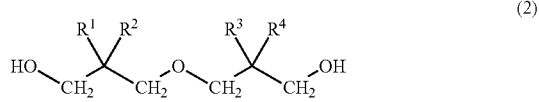

(2)

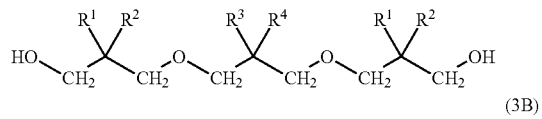

(3A)

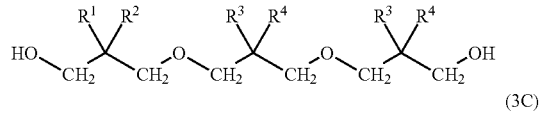

(3B)

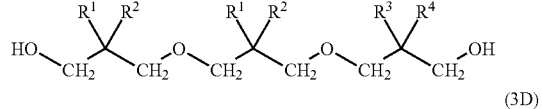

(3C)

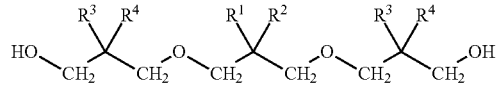

(3D)

wherein in the formulae (1), (2), (3A), (3B), (3C), and (3D), $R^1$, $R^2$, $R^3$, and $R^4$ may be the same or different, and represent a linear or branched alkyl group having 1 to 6 carbon atoms; and in each of $R^1$, $R^2$, $R^3$, and $R^4$, independently, one or two or more hydrogen atoms contained in the alkyl group may be replaced with an alkoxy group having 6 or less carbon atoms or a functional group inactive for a hydrogenation reduction reaction.

[2] The method described above, wherein the polyether diol is a compound represented by the general formula (2).

[3] The method described above, wherein the polyether diol is at least one compound selected from the group consisting of the compounds represented by the general formulae (3A), (3B), (3C), and (3D).

[4] The method described above, wherein the polyether diol is obtained with at least one polyether diol selected from the group consisting of by-produced polyether diols having 4 or more and 9 or less neo skeletons in a molecule.

[5] The method described above, wherein at least a part of the compound represented by the general formula (1) is subjected to self-condensation, and thereafter hydrogenation reduction.

[6] The method described above, wherein $R^1$ and $R^3$ are the same group, and $R^2$ and $R^4$ are the same group.

[7] The method described above, wherein $R^1$ and $R^2$ are the same group, or $R^3$ and $R^4$ are the same group.

[8] The method described above, wherein $R^1$ and $R^2$ are different groups, or $R^3$ and $R^4$ are different groups.

[9] The method described above, wherein $R^1$, $R^2$, $R^3$, and $R^4$ are, in this order, a methyl group, a methyl group, a methyl group, and a methyl group; a methyl group, a methyl group, a methyl group, and an ethyl group; a methyl group, a methyl group, a methyl group, and a normal propyl group; a methyl group, a methyl group, a methyl group, and a normal butyl group; a methyl group, a methyl group, a methyl group, and a normal hexyl group; a methyl group, a methyl group, an ethyl group, and an ethyl group; a methyl group, a methyl group, an ethyl group, and a normal butyl group; a methyl group, a methyl group, a normal propyl group, and a normal pentyl group; a methyl group, an ethyl group, a methyl group, and an ethyl group; an ethyl group, an ethyl group, an ethyl group, and an ethyl group; a methyl group, a normal propyl group, a methyl group, and a normal propyl group; a methyl group, a normal butyl group, a methyl group, and a normal butyl group; a methyl group, a normal hexyl group, a methyl group, and a normal hexyl group; an ethyl group, a normal butyl group, an ethyl group, and a normal butyl group; or a normal propyl group, a normal pentyl group, a normal propyl group, and a normal pentyl group.

[10] The method described above, wherein both $R^1$ and $R^2$ are methyl groups, or both $R^3$ and $R^4$ are methyl groups.

[11] The method described above, wherein all of $R^1$, $R^2$, $R^3$, and $R^4$ are methyl groups.

[12] The method described above, wherein the compound represented by the general formula (1) is subjected to hydrogenation reduction in a system containing an ether compound or a saturated hydrocarbon compound which is a reaction solvent.

[13] The method described above, wherein the hydrogenation catalyst is a solid catalyst containing at least one selected from the group consisting of palladium, platinum, nickel, and copper.

[14] The method described above, wherein the hydrogenation catalyst is a solid catalyst containing a zirconium compound or an apatite compound.

[15] A polyether diol represented by the following general formula (A):

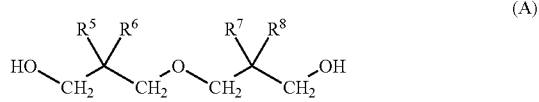

wherein in the formula (A), $R^5$, $R^6$, $R^7$, and $R^8$ each independently represent a linear or branched alkyl group having 1 to 6 carbon atoms; in each of $R^5$, $R^6$, $R^7$, and $R^8$, independently, one or two or more hydrogen atoms contained in the alkyl group may be replaced with an alkoxy group having 6 or less carbon atoms or a functional group inactive for a hydrogenation reduction reaction; and at least one of $R^5$ and $R^6$ is a different group from at least one of $R^7$ and $R^8$.

[16] The polyether diol described above, wherein $R^5$ and $R^6$ are different groups, or $R^7$ and $R^8$ are different groups.

[17] The polyether diol described above, wherein both $R^5$ and $R^6$ are methyl groups, or both $R^7$ and $R^8$ are methyl groups.

[18] A polyether diol represented by the following general formula (B1) or (B2):

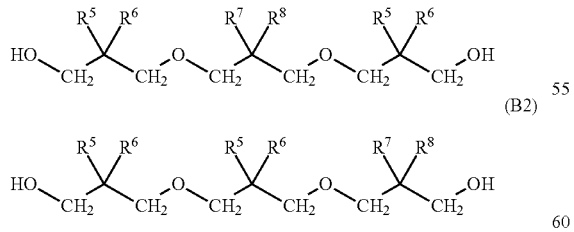

wherein in the formulae (B1) and (B2), $R^5$, $R^6$, $R^7$, and $R^8$ each independently represent a linear or branched alkyl group having 1 to 6 carbon atoms; in each of $R^5$, $R^6$, $R^7$, and $R^8$, independently, one or two or more hydrogen atoms contained in the alkyl group may be replaced with an alkoxy group having 6 or less carbon atoms or a functional group inactive for a hydrogenation reduction reaction; and at least one of $R^5$ and $R^6$ is a different group from at least one of $R^7$ and $R^8$.

[19] The polyether diol described above, wherein $R^5$ and $R^6$ are different groups, or $R^7$ and $R^8$ are different groups.

[20] The polyether diol described above, wherein both $R^5$ and $R^6$ are methyl groups, or both $R^7$ and $R^8$ are methyl groups.

A producing method of the present invention can efficiently produce a polyether diol. A novel polyether diol having a low melting point can be obtained.

DESCRIPTION OF EMBODIMENTS

Figure 1:
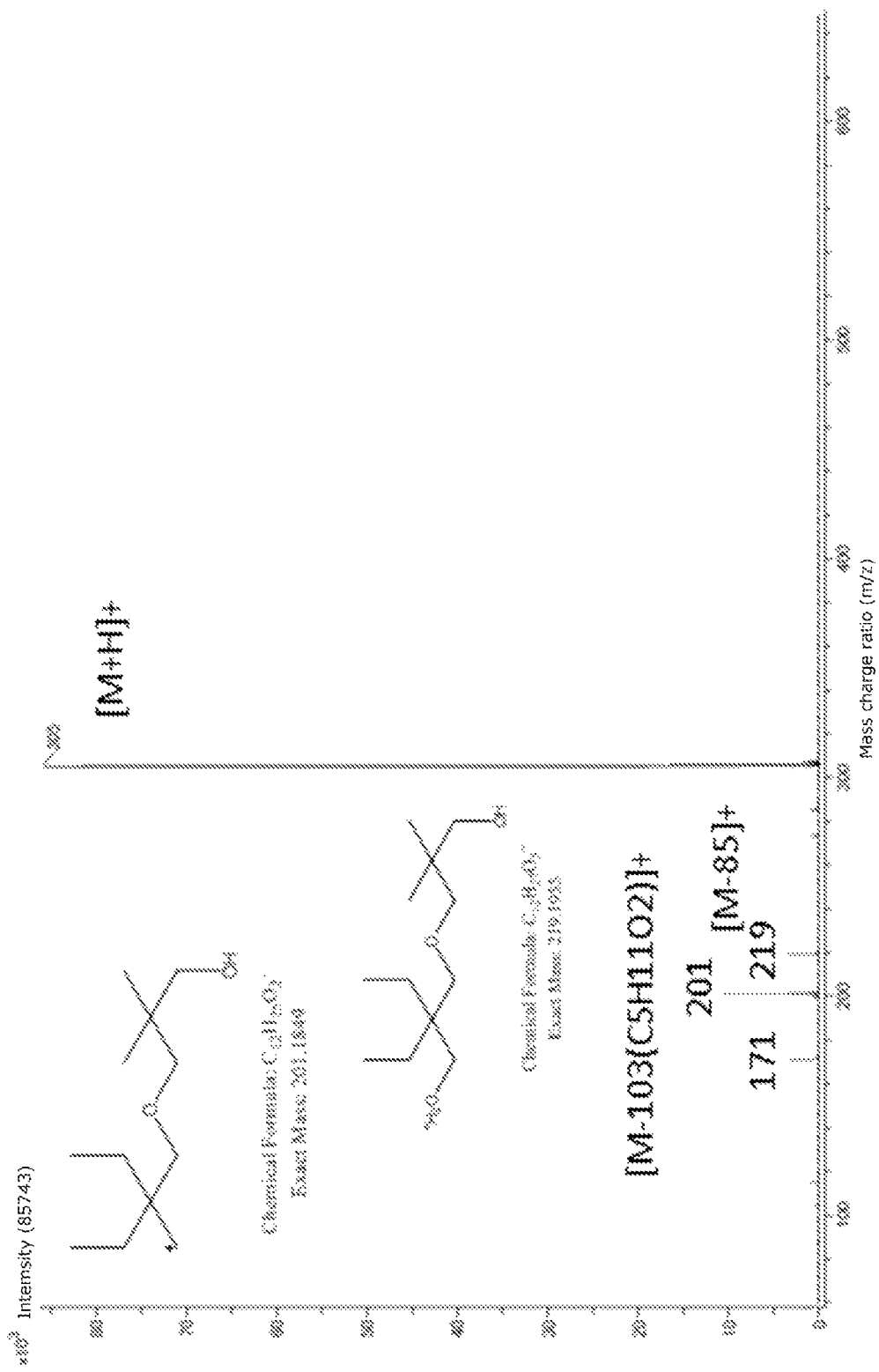
FIG. 1 is an MS spectrum of a compound MMEEMM.

Hereinafter, embodiments of the present invention (hereinafter, simply referred to as a "present embodiment") will be described. The present embodiment below is exemplification for describing the present invention, and the present invention is not limited to only the present embodiment. A method for producing a polyether diol of the present embodiment is a method including the step of subjecting a compound represented by the following general formula (1) to hydrogenation reduction in the presence of a hydrogenation catalyst to provide at least one polyether diol selected from the group consisting of compounds represented by the following general formulae (2), (3A), (3B), (3C), and (3D).

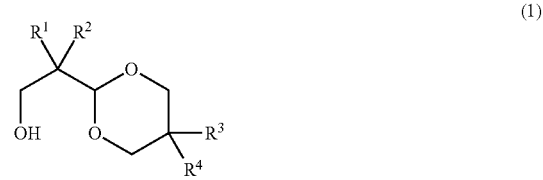

(1)

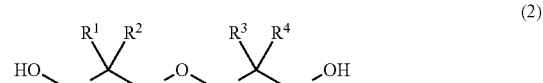

(2)

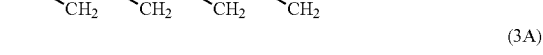

(3A)

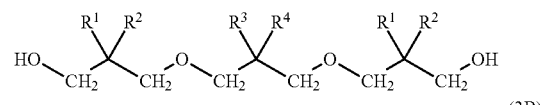

(3B)

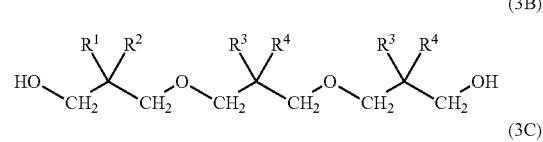

(3C)

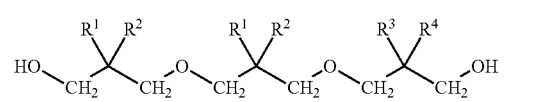

(3D)

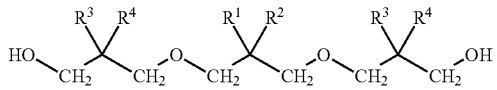

Herein, in the formulae (1), (2), (3A), (3B), (3C), and (3D), $R^1$, $R^2$, $R^3$, and $R^4$ may be the same or different, and represent a linear or branched alkyl group having 1 to 6 carbon atoms, and in each of $R^1$, $R^2$, $R^3$, and $R^4$, independently, one or two or more hydrogen atoms contained in the alkyl group may be replaced with an alkoxy group having 6 or less carbon atoms or a functional group inactive for a hydrogenation reduction reaction. When $R^1$ and $R^2$ are different, and/or when $R^3$ and $R^4$ are different, a plurality of geometric isomers and optical isomers may be present.

<Raw Material Compound>

A compound used as a raw material for a method for producing a polyether diol of the present embodiment (hereinafter, also merely referred to as a "producing method") is a six-membered ring acetal compound (hereinafter, referred to as a "compound (1)") having a 1,3-dioxane skeleton represented by the general formula (1).

A synthetic raw material and a producing method or the like of the compound (1) used for the present embodiment are not particularly limited, and a compound produced by a conventionally known method can be used. The producing method of the compound (1) which is simplest and efficient is a method for subjecting 3-hydroxy-2,2-disubstituted-propionaldehyde and 2,2-disubstituted-1,3-propanediol to cyclodehydration using an acid catalyst or the like. Apart from this, the producing method may be based on an acetal exchange reaction between a lower alcohol acetal of 3-hydroxy-2,2-disubstituted-propionaldehyde, and 2,2-disubstituted-1,3-propanediol. Alternatively, the compound (1) may be by-produced from a producing process of 3-hydroxy-2,2-disubstituted-propionaldehyde and 2,2-disubstituted-1,3-propanediol. The refined compound (1) can be used as a raw material compound for the producing method of the present embodiment.

Examples of 3-hydroxy-2,2-disubstituted-propionaldehyde which can be employed when the compound (1) is produced by subjecting 3-hydroxy-2,2-disubstituted-propionaldehyde and 2,2-disubstituted-1,3-propanediol to cyclodehydration include 3-hydroxy-2,2-dimethyl-propionaldehyde, 3-hydroxy-2,2-diethyl-propionaldehyde, 3-hydroxy-2-methyl-2-ethyl-propionaldehyde, 3-hydroxy-2-methyl-2-propyl-propionaldehyde, 3-hydroxy-2-methyl-2-butyl-propionaldehyde, 3-hydroxy-2-ethyl-2-butyl-propionaldehyde, 3-hydroxy-2-propyl-2-pentyl-propionaldehyde, and 3-hydroxy-2-methyl-2-hexyl-propionaldehyde. Substituent groups bonded to a carbon atom at 2-position of a propionaldehyde skeleton correspond to $R^1$ and $R^2$ in the general formula (1).

Examples of 2,2-disubstituted-1,3-propanediol which can be applied in this case include 2,2-dimethyl-1,3-propanediol, 2,2-diethyl-1,3-propanediol, 2-methyl-2-ethyl-1,3-propanediol, 2-methyl-2-propyl-1,3-propanediol, 2-methyl-2-butyl-1,3-propanediol, 2-ethyl-2-butyl-1,3-propanediol, 2-propyl-2-pentyl-1,3-propanediol, and 2-methyl-2-hexyl-1,3-propanediol. Substituent groups bonded to a carbon atom at 2-position of 1,3-propanediol correspond to $R^3$ and $R^4$ in the general formula (1).

The polyether diol obtained in the producing method of the present embodiment is at least one compound selected from the group consisting of compounds represented by the following general formulae (2), (3A), (3B), (3C), and (3D).

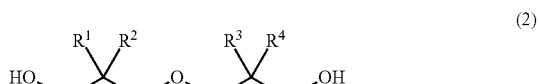

(2)

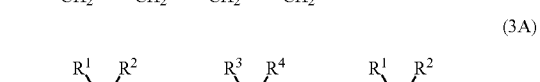

(3A)

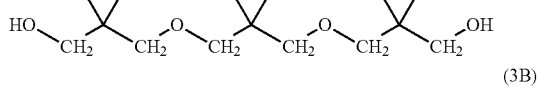

(3B)

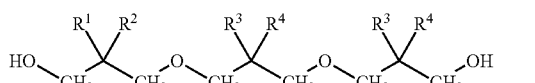

(3C)

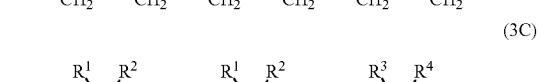

(3D)

Herein, in the formulae (2), (3A), (3B), (3C), and (3D), $R^1$, $R^2$, $R^3$, and $R^4$ have the same meanings as those in the general formula (1).

One of the polyether diols obtained by the producing method of the present embodiment is obtained by adding only one hydrogen molecule to the compound (1), and is represented by the general formula (2). Hereinafter, for the sake of simplicity, the polyether diol is abbreviated to a "compound (2)."

The present inventors considered a hydrogenation reduction reaction of the compound (1) in detail, and found that not only the compound (2) but also at least one of polyether diols (hereinafter, these are collectively abbreviated to a "compound (3)") represented by the general formulae (3A), (3B), (3C), and (3D) are simultaneously generated in no small measure.

From the observation of the compound (3) by the present inventors, the amount of the compound (2) to be generated is always more than that of the compound (3). A consecutive reaction from the compound (2) is presumed to generate the compound (3) although the exact reaction mechanism is unclear.

As apparent from the above, the producing method of the present embodiment can be said to be also a producing method of a mixture of the polyether diols. Herein, the mixture of the polyether diols means not a mixture containing all these various product materials but a mixture containing the compound (2) and at least one selected from the compound (3).

Examples of $R^1$, $R^2$, $R^3$, and $R^4$ in the general formula (1) include a methyl group, an ethyl group, a n-propyl group, a 1-methyl ethyl group (isopropyl group), a n-butyl group, a 1-methyl propyl group, a 2-methyl propyl group, a 1,1-dimethyl ethyl group (tert-butyl group), a n-pentyl group, a 1-methyl butyl group, a 2-methyl butyl group, a 3-methyl butyl group, a 1-ethyl propyl group, a 1,1-dimethyl propyl group, a 1,2-dimethyl propyl group, a 2,2-dimethyl propyl group (neopentyl group), a n-hexyl group, a 1-methyl pentyl group, a 2-methyl pentyl group, a 3-methyl pentyl group, a 4-methyl pentyl group, a 1,1-dimethyl butyl group, a 1,2-dimethyl butyl group, a 1,3-dimethyl butyl group, a 2,2-dimethyl butyl group, a 2,3-dimethyl butyl group, a 3,3-dimethyl butyl group, a 1-ethyl butyl group, a 2-ethyl butyl group, a 1,1,2-trimethyl propyl group, a 1,2,2-trimethyl propyl group, a 1-ethyl-1-methyl propyl group, and a 1-ethyl-2-methyl propyl group.

Examples of alkoxy groups which one or two or more hydrogen atoms contained in the alkyl group of $R^1$, $R^2$, $R^3$, and $R^4$ in the general formula (1) may be replaced with and have 6 or less carbon atoms include a methoxy group, an ethoxy group, a n-propoxy group, a 1-methyl ethoxy group (isopropoxy group), a n-butoxy group, a 1-methyl propoxy group, a 2-methyl propoxy group, a 1,1-dimethyl ethoxy group (tert-butoxy group), a n-pentoxy group, a 2-methyl butoxy group, a n-hexoxy group, and a 2-methyl pentoxy group. Furthermore, examples of functional groups in which one or two or more hydrogen atoms contained in the alkyl group in $R^1$, $R^2$, $R^3$, and $R^4$ may be replaced with and are inactive for a hydrogenation reduction reaction include a chlorinated alkyl group such as a chloro group or a methyl chloro group, and an alkyl fluoride group such as a fluoro group or a methyl fluoro group.

In the compound (1), when $R^1$ and $R^3$ are the same group, and $R^2$ and $R^4$ are the same group, the generated compound is a polyether diol having a single neo skeleton, and is represented by the following simple general formulae (2E) and (3E).

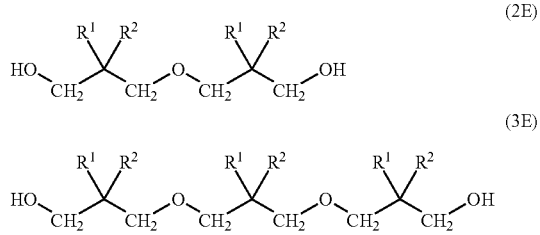

Furthermore, when all of $R^1$, $R^2$, $R^3$, and $R^4$ are the same substituent groups in the compound (1), the compound (1) is a simpler compound. For example, when each of $R^1$, $R^2$, $R^3$, and $R^4$ is a methyl group, the compound (2) is 3-(3-hydroxy-2,2-dimethyl-propoxy)-2,2-dimethyl-propane-1-ol, and the compound (3) is 3-[3-(3-hydroxy-2,2-dimethyl-propoxy)-2,2-dimethyl-propoxy]-2,2-dimethyl-propane-1-ol.

On the other hand, when at least one of $R^1$ and $R^2$ is a different group from at least one of $R^3$ and $R^4$ in the compound (1), the generated compound is a polyether diol having a plurality of neo skeletons.

Irrespective of whether a single or a plurality of neo skeletons are included in the compound (2) and the compound (3), $R^1$ and $R^2$ may be the same group, or $R^3$ and $R^4$ may be the same group. In this case, both $R^1$ and $R^2$ may be methyl groups, or both $R^3$ and $R^4$ may be methyl groups. $R^1$ and $R^2$ may be different groups, or $R^3$ and $R^4$ may be different groups.

Examples of $R^1$, $R^2$, $R^3$, and $R^4$ include, in this order, a methyl group, a methyl group, a methyl group, and a methyl group; a methyl group, a methyl group, a methyl group, and an ethyl group; a methyl group, a methyl group, a methyl group, and a normal propyl group; a methyl group, a methyl group, a methyl group, and a normal butyl group; a methyl group, a methyl group, a methyl group, and a normal hexyl group; a methyl group, a methyl group, an ethyl group, and an ethyl group; a methyl group, a methyl group, an ethyl group, and a normal butyl group; a methyl group, a methyl group, a normal propyl group, and a normal pentyl group; a methyl group, an ethyl group, a methyl group, and an ethyl group; an ethyl group, an ethyl group, an ethyl group, and an ethyl group; a methyl group, a normal propyl group, a methyl group, and a normal propyl group; a methyl group, a normal butyl group, a methyl group, and a normal butyl group; a methyl group, a normal hexyl group, a methyl group, and a normal hexyl group; an ethyl group, a normal butyl group, an ethyl group, and a normal butyl group; and a normal propyl group, a normal pentyl group, a normal propyl group, and a normal pentyl group.

When the polyether diol thus obtained is a mixture containing a plurality of compounds, the polyether diol can be utilized as-is, as an industrial raw material such as a resin, a coating material, or an adhesive, or individual compounds into which the polyether diol is separated by using a conventionally known separation technique such as adsorption, extraction, distillation, or crystallization can be utilized as the industrial raw material.

Japanese Patent No. 2977782 discloses a method for producing an ether-monoalcohol compound by subjecting a cyclic acetal compound having a specific 1,3-dioxane structure to hydrogenation reduction to ring-open the cyclic acetal compound. The cyclic acetal compound is synthesized from a carbonyl compound and a 1,3-propane diol compound.

In the meantime, there is generally widely known a reaction in which an aliphatic alcohol compound is subjected to hydrogenolysis on a hydrogenation catalyst to reductively desorb a hydroxyl group (see the following formula)

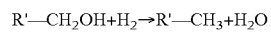

Herein R' represents a residue.

This reaction is apt to occur as the aliphatic alcohol compound has more hydroxyl groups in a molecule. When the aliphatic alcohol compound is a polyhydric alcohol, the reaction remarkably occurs. For example, Japanese Patent Application Laid-Open Nos. 2009-173551 and 2010-111618 disclose that a primary hydroxyl group of a polyhydric alcohol compound is easily subjected to hydrogenolysis in the presence of a catalyst in which a metal component having a hydrogenation property such as copper or a platinoid element is supported on zeolite or silica. In light of the disclosure, in the present invention, the number of the primary hydroxyl groups in the acetal compound which is a raw material and the number of the primary hydroxyl groups in the alcoholic compound which is a product material are more, by one, than that in the method described in Japanese Patent No. 2977782. In addition, it is surprising that a high reaction selectivity is obtained although the product material is the polyether diol, i.e., the polyhydric alcohol.

The present inventors considered a hydrogenation reaction in detail, and found that the presence or absence of the primary hydroxyl group of the acetal compound which is a raw material greatly affects reaction selectivity. That is, when the acetal compound as the raw material has the primary hydroxyl group as in the present invention, a polymer-like side product was generated under the absence of hydrogen gas in the reaction system or under a condition that a hydrogen pressure is extremely low. This is considered to be because a reaction caused by an acetal exchange reaction proceeds between the molecules of the acetal compound which is the raw material, or with the polyether diol partially generated. Therefore, when the acetal compound which is the raw material has at least one hydroxyl group, it is necessary to avoid or suppress the generation of the polymer-like side product, or achieve the desired hydrogenation reaction at a reaction rate exceeding the generation of the polymer-like side product, in order to improve the yield of the desired polyether diol. Thus, the present invention has a very large technical sense of a primary hydroxyl group being present in the molecule of the acetal compound which is the raw material, and high technical difficulty required for the hydrogenation reaction.

The present inventors have confirmed that a polymerization reaction hardly occurs in an experiment using a cyclic acetal compound (2-tertiary butyl-5,5-dimethyl-[1,3]dioxane) of pivalaldehyde-neopentyl glycol when the acetal compound as the raw material has no primary hydroxyl group as described in Japanese Patent No. 2977782.

The present inventors presume that the compounds represented by the general formulae (3A), (3B), (3C), and (3D) in the polyether diol obtained in the present invention are generated by subjecting the above-mentioned polymer-like side product to the hydrogenation reduction in no small measure. That is, at least a part of the compound represented by the general formula (1) may be subjected to self-condensation, and thereafter hydrogenation reduction, to obtain the polyether diol. The compounds represented by the general formulae (3A), (3B), (3C), and (3D) are not limited to the compounds thus generated.

When the compounds represented by the general formulae (2), (3A), (3B), (3C), and (3D), particularly the compounds represented by the general formulae (3A), (3B), (3C), and (3D) are generated in a relatively large amount, the present inventors confirm also the production of a 1,3-propanediol compound having one neo skeleton derived from the general formula (1) and a higher polyether diol having 4 or more neo skeletons in a molecule. The production of largest polyether diol having 9 neo skeletons in a minute amount is confirmed by mass spectrometry. However, the amount of the polyether diol having 4 or more neo skeletons in the molecule to be generated is not very large. The yield of such higher polyether diol is 5% or less in total based on the neo skeleton of a feed raw material in most cases. The higher polyether diol is obtained as a mixture with product materials such as the compounds represented by the general formulae (2), (3A), (3B), (3C), and (3D). That is, the present invention includes also a method for producing a polyether diol, including the step of subjecting the compound represented by the general formula (1) to the hydrogenation reduction in the presence of the hydrogenation catalyst, to obtain at least one polyether diol selected from the group consisting of the compounds represented by the general formulae (2), (3A), (3B), (3C), and (3D), and at least one polyether diol selected from the group consisting of by-produced polyether diols having 4 or more and 9 or less neo skeletons in a molecule.

On the other hand, when the acetal compound which is the raw material has no primary hydroxyl group, the polymerization reaction hardly proceeds, and the amount of the polyether diol having three neo skeletons to be generated is only the trace amount. The polyether diol having 4 or more neo skeletons is not observed.

From the above, the technical difficulty required for the hydrogenation reduction reaction of the present invention in which the primary hydroxyl group is increased in the acetal compound which is the raw material and the generated alcoholic compound is higher than that of the technique described in Japanese Patent No. 2977782. It is surprising that a high reaction selectivity is obtained in the present invention.

The present inventors also considered a compound partially containing a neo skeleton as an analog of the compound (1). However, as shown in Comparative Examples to be described later, when the compound is used, an intense decomposition reaction occurs, and the desired polyether diol is obtained only in a small amount. When an alkyl substituent group such as an isopropyl group is introduced into a methylene group ($—CH_2—$) being adjacent to the quaternary carbon of the neo skeleton as the analog of the compound (1), although the reaction proceeds, the reaction rate is extremely slow and the reaction selectivity is also significantly decreased. Although the desired polyether diol is generated, a sufficient yield is not obtained.

<Hydrogenation Catalyst>

Examples of active ingredients of the hydrogenation catalyst used in the present embodiment include a metal element having a catalytic hydrogenation property (hereinafter, referred to as a "specific metal component"). Examples of the specific metal component include nickel, cobalt, iron, ruthenium, rhodium, palladium, platinum, iridium, copper, silver, molybdenum, tungsten, chromium, and rhenium. As long as the specific metal component exhibits a hydrogenation property, the specific metal component may be in a metal state or in a cation state. Among these, since the hydrogenation property of the specific metal component in the metal state is generally higher, and the specific metal component is more stable under a reduction atmosphere, the specific metal component is preferably in the metal state. The specific metal components may be used either singly or in combinations of two or more in a state where the specific metal components are contained in a solid catalyst. When the two or more specific metal components are used, the combination, mixing ratio, and form of the specific metal components are not particularly limited, and the specific metal components may be used in a form such as a mixture, alloy or intermetallic compound of metals. In the present embodiment, the hydrogenation catalyst is preferably a solid catalyst containing at least one selected from the group consisting of palladium, platinum, nickel, and copper, and particularly preferably a solid catalyst containing palladium.

Raw materials of the specific metal components are not particularly limited. Raw materials used when the catalyst is prepared by a conventionally known method can be employed. Examples of the raw materials include hydroxides, oxides, fluorides, chlorides, bromides, iodides, sulfates, nitrates, acetates, ammine complexes, and carbonyl complexes of metal elements. These are used either singly or in combinations of two or more.

In the hydrogenation catalyst of the present embodiment, the specific metal component as the metal component may also be used either singly or in combinations with a metal having no catalytic hydrogenation property. Examples of the hydrogenation catalyst include a catalyst such as palladium black or platinum black including a metal fine powder of the specific metal component, and a sponge catalyst prepared by forming an alloy from the specific metal component, aluminum, and a small amount of additive, and thereafter leaching all or part of aluminum.

In order to further improve the activity, selectivity, and physical properties or the like of the catalyst, the specific metal component and the following components may also be added to the catalyst and used: lithium, sodium, potassium, rubidium, and cesium as an alkali metal element; magnesium, calcium, strontium, and barium as an alkaline-earth metal element; fluoride, chlorine, bromine, and iodine as a halogen element; and a compound of one or two or more elements selected from the group consisting of mercury, lead, bismuth, tin, tellurium, and antimony as an auxiliary added element (hereinafter, abbreviated to a specific addition component).

Raw materials of these specific addition components are not particularly limited. Raw materials used when the catalyst is prepared by a conventionally known method can be employed. Examples of the raw materials include hydroxides, oxides, fluorides, chlorides, bromides, iodides, sulfates, nitrates, acetates, and ammine complexes of metal elements. These are used either singly or in combinations of two or more. An addition method of the specific addition component, and a ratio of the specific addition component to the specific metal component are not also particularly limited.

In the hydrogenation catalyst of the present embodiment, the specific metal component may also be used in combination with a non-metal substance. Main examples of the non-metal substance include an elementary substance, carbide, nitride, oxide, hydroxide, sulfate, carbonate, and phosphate (hereinafter, referred to as a "specific non-metal component"). Specific examples thereof include graphite, diamond, activated carbon, silicon carbide, silicon nitride, aluminum nitride, boron nitride, boron oxide, aluminum oxide (alumina), silicon oxide (silica), titanium oxide, zirconium oxide, hafnium oxide, lanthanum oxide, cerium oxide, yttrium oxide, niobium oxide, magnesium silicate, calcium silicate, magnesium aluminate, calcium aluminate, zinc oxide, chromic oxide, alumino silicate, aluminosilico phosphate, alumino phosphate, borophosphate, magnesium phosphate, calcium phosphate, strontium phosphate, apatite hydroxide (hydroxy calcium phosphate), apatite chloride, apatite fluoride, calcium sulfate, barium sulfate, and barium carbonate. The specific non-metal component is used either singly or in combinations of two or more. When the specific non-metal components are used in combinations of two or more, the combination, mixing ratio, and form of the specific non-metal components are not particularly limited, and the specific non-metal components may be used in a form such as a mixture, composite compound, or double salt of compounds.

From the viewpoint of industrial use, a specific non-metal component obtained simply and inexpensively is preferable. The specific non-metal component is preferably a zirconium compound, an aluminum compound, and an apatite compound, and more preferably a zirconium compound and an apatite compound. Among these, the specific non-metal component is particularly preferably zirconium oxide and apatite hydroxide (hydroxy calcium phosphate). Furthermore, a part or all of these specific non-metal components to be used may be modified or ion-exchanged by using the above-mentioned specific addition component.

Carbide, nitride, and oxide or the like of the specific metal component can be used as the specific non-metal component. When these are exposed to a hydrogenation reduction atmosphere, a part thereof is reduced to a metal. In such a case, a part thereof is used as the specific metal component, and the rest is used as the non-metal component. Examples in the case include oxides such as nickel oxide, iron oxide, cobalt oxide, molybdenum oxide, tungstic oxide, and chromic oxide.

The specific metal component may be singly used as the hydrogenation catalyst of the present embodiment; the specific metal component and the specific non-metal component may be used in combination; and the hydrogenation catalyst may contain the specific addition component, besides these, in some cases. The producing method of the hydrogenation catalyst of the present embodiment is not particularly limited, and a conventionally known method can be used. Examples thereof include a method for impregnating the specific non-metal component with the raw material compound of the specific metal component (supporting method), a method for dissolving both the raw material compound of the specific metal component and the raw material compound of the specific non-metal component in a suitable solvent, and simultaneously depositing the specific metal component and the specific non-metal component by using an alkali compound or the like (coprecipitation method), and a method for mixing and uniformizing the raw material compound of the specific metal component and the specific non-metal component at a suitable ratio (kneading method).

Depending on the composition of the hydrogenation catalyst or the convenience of the catalyst preparation method, the specific metal component can be prepared in a cation state, and then reduced to bring the specific metal component into a metal state. A conventionally known reduction method and reducing agent can be used therefor, and are not particularly limited. Examples of the reducing agent include reducing inorganic gas such as hydrogen gas, carbon monoxide gas, ammonia, hydrazine, phosphine, or silane, a lower oxygen-containing compound such as methanol, formaldehyde, or formic acid, and hydride such as sodium boron hydride or aluminum lithium hydride. The specific metal component is changed to the metal state by reducing the specific metal component in the cation state in a gas phase or a liquid phase in which these reducing agents are present. The reduction processing condition at this time can be set to a suitable condition depending on the kinds and quantities or the like of the specific metal component and reducing agent. The reduction processing may be separately operated by using a catalyst reduction equipment before the hydrogenation reduction in the producing method of the present embodiment, or may be operated before reaction start or simultaneously with reaction operation, in a reactor vessel used for the producing method of the present embodiment.

The metal content and shape of the hydrogenation catalyst of the present embodiment are not also particularly limited. In terms of the shape, the hydrogenation catalyst may be a powder or may be molded. The shape of the molded hydrogenation catalyst and the molding method are not particularly limited. For example, a spherical product, a tablet molded product, and an extrusion molded product, and a product obtained by crushing those products to a suitable size may be appropriately selected and used.

The specific metal component is particularly preferably palladium. Hereinafter, a catalyst including palladium will be described in detail. When the specific metal component is palladium, considering that palladium is a noble metal, it is economically desired that the amount of palladium to be used is small, and palladium is effectively utilized. Therefore, it is preferable that palladium is used in a state where it is dispersibly supported on a catalyst carrier.

A palladium compound as a raw material of palladium is suitably a palladium compound which is soluble in water or an organic solvent. Examples of the palladium compound include palladium chloride, a tetrachloropalladium salt, a tetraamminepalladium salt, palladium nitrate, and palladium acetate. Among these, palladium chloride is preferable as it has high solubility in water or an organic solvent and is likely to be industrially utilized. Palladium chloride can be used after dissolved in an aqueous solution of sodium chloride, diluted hydrochloric acid, and ammonia water or the like.

The solution of the palladium compound is added to the catalyst carrier, or the catalyst carrier is immersed in the solution of the palladium compound, to fix palladium or the palladium compound on the catalyst carrier. General examples of the fixing method include adsorption to a carrier, crystallization by removing a solvent by distillation, and precipitation-deposition using a reducing substance and/or a basic substance acting on the palladium compound. A suitable method is appropriately used for the fixing method. The content of palladium in the hydrogenation catalyst prepared by the method is preferably 0.01 to 20% by mass, more preferably 0.1 to 10% by mass, and still more preferably 0.5 to 5% by mass in terms of metal palladium based on the total amount of the hydrogenation catalyst. When the content of palladium is 0.01% by mass or more, a more sufficient hydrogenation rate is obtained, and the conversion of the compound (1) is further increased. On the other hand, when the content of palladium is 20% by mass or less, dispersion efficiency of palladium in the hydrogenation catalyst is further increased, and palladium can be more effectively used.

Depending on the convenience of the palladium compound or the catalyst preparation method, palladium may be supported on the carrier not in a metal state but in a cation state. In that case, supported palladium as a cation (for example, present in a state of the palladium compound) can also be used after being reduced to metal palladium. A conventionally known reduction method and reducing agent can be employed therefor, and are not particularly limited. Examples of the reducing agent include reducing inorganic gases such as hydrogen gas, carbon monoxide gas, ammonia, and hydrazine, lower oxygen-containing compounds such as methanol, formaldehyde, and formic acid, hydrocarbon compounds such as ethylene, propylene, benzene, and toluene, and hydrides such as sodium boron hydride and aluminum lithium hydride. Palladium as the cation can be easily reduced to metal palladium by bringing palladium into contact with the reducing agent in a gas phase or a liquid phase. The reduction processing condition at this time can be set to a suitable condition by the kind and quantity or the like of the reducing agent. The reduction processing may be separately operated by using a catalyst reduction equipment before the hydrogenation reduction in the producing method of the present embodiment, or may be operated before reaction start or simultaneously with reaction operation in a reactor vessel used for the producing method of the present embodiment.

One kind of the specific non-metal component used with the specific metal component of the present invention is preferably a zirconium compound. The hydrogenation catalyst containing the zirconium compound will be described in detail later. The zirconium compound used for the present embodiment is preferably obtained by using one selected from the group consisting of zirconium oxide, zirconium hydroxide, zirconium carbonate, alkaline earth zirconate salts, rare earth zirconate salts, and zircon, alone or a combination of two or more thereof.

The zirconium compound is particularly preferably zirconium oxide, and a method for producing zirconium oxide is not particularly limited. For example, a method for decomposing an aqueous solution of a soluble zirconium salt by a basic substance to produce zirconium hydroxide or zirconium carbonate, and thereafter thermally decomposing zirconium hydroxide or zirconium carbonate to prepare zirconium oxide is known as a general method. Examples of raw materials of the zirconium compound at this time include, but are not limited to, zirconium oxychloride, zirconium oxynitrate, zirconium chloride, zirconium sulfate, zirconium tetraalkoxide, zirconium acetate, and zirconium acetylacetonato. These are used either singly or in combinations of two or more. Examples of the basic substance used for decomposition include ammonia, alkylamines, ammonium carbonate, ammonium hydrogen carbonate, sodium hydroxide, sodium carbonate, sodium hydrogen carbonate, potassium hydrate, potassium carbonate, potassium hydrogen carbonate, manganese hydroxide, calcium hydroxide, lanthanum hydroxide, yttrium hydroxide, and cerium hydroxide. These are used either singly or in combinations of two or more.

When zirconium oxide is used as the specific non-metal component, the physical properties and shape thereof are not particularly limited. The purity of zirconium oxide is not also particularly limited, and a commercially available general-purpose product and a high purity product can be appropriately used.

Another kind of the specific non-metal component used with the specific metal component of the present embodiment is preferably an apatite compound. The hydrogenation catalyst containing the apatite compound will be described in detail later. Examples of the apatite compound used for the present embodiment include a hexagonal compound having a composition of $M_{10}(ZO_4)_6X_2$ described in the academic journal "Syokubai (Catalysts & Catalysis)," 27 (4), 237-243 (1985). Herein, examples of M include calcium, strontium, aluminum, yttrium, lanthanum, and cerium. Examples of Z include phosphorus, arsenic, vanadium, and chromium. Examples of X include a hydroxyl group, a carbonate group, fluoride, chlorine, bromine, and iodine. All of M, Z, and X may contain one or two or more of the above within a range of restriction on a physical structure by an ion radius or the like. The apatite compound is also known to have a non-stoichiometric composition. The apatite compound of the present embodiment includes also the non-stoichiometric composition. The non-stoichiometric composition is represented by the general formula of $M_{10-a}(HZO_4)_a(ZO_4)_{6-a}X_{2-a}$ where $0<a\leq1$ is set.

Among these, it is preferable that M is calcium and Z is phosphorus. The producing method of the apatite compound having calcium and phosphorus is not particularly limited, and a conventionally known method can be used. Examples of the method include a method for sufficiently mixing a suitable phosphate and calcium salt at a stoichiometric ratio, and thereafter heating them (solid phase method), a method for mixing a calcium cation-containing solution and a phosphate anion-containing solution under a basic condition to obtain a precipitation (precipitation method), a method for hydrolyzing calcium phosphate having poor water solubility as a starting material under a basic condition to convert calcium phosphate into apatite (hydrolysis method), and a method for hydrothermally processing calcium phosphate having poor water solubility in a sealing pressure tight case (hydrothermal synthesis method). A suitable method is appropriately employed.

The apatite compound has anion exchangeability. It is known that a portion equivalent to X can be easily anion-exchanged even after being synthesized as the apatite compound. The apatite compound of the present embodiment includes calcium phosphate apatite having one or two or more anions such as a carbonate group, a bicarbonate group, a hydroxyl group, chloride, and fluoride, and having a part or all thereof exchanged with anions different from that during synthesizing. At least a part of anions of the apatite compound may be exchanged by, for example, a method for synthesizing hydroxylated calcium phosphate, and bringing a solution containing chloride or fluoride ions into contact therewith, and a method for bringing anions contained as a part of raw materials of a specific metal component or a specific addition component into contact with the apatite compound when supporting a specific metal component or a specific addition component on the apatite compound used as a carrier. A starting material in ion exchange treatment at this time, a concentration, and a processing condition or the like are not particularly limited. A suitable method is appropriately used.

When the specific non-metal component typified by the zirconium compound and the apatite compound is used as the catalyst carrier, the shapes and values of physical properties such as particle diameters and porosities of these carriers, and a method for supporting a metal component, or the like are not particularly limited. A shape suitable for a reaction method and a condition, physical properties of the carrier, and a support method or the like can be appropriately selected and used.

For the solvent used for the hydrogenation reduction of the present embodiment, a reaction may be performed under a non-solvent environment using only the compound (1) which is the raw material, or a reaction solvent may be used. When the reaction solvent to be used is in a state inactive for hydrogenation reduction, the kind and concentration thereof are not particularly limited. However, when a reaction solvent having higher interaction with the specific metal component in the hydrogenation catalyst than that of the compound (1) is used, the reaction rate may be extremely decreased or the reaction may stop. From the viewpoint, it is preferable that a compound containing, for example, phosphorus, nitrogen, and sulfur is not used as the reaction solvent. However, the reaction solvent may be used in an amount small enough that it does not greatly influence the reaction rate. The reaction solvent is preferably a saturated hydrocarbon, an ester compound, and an ether compound. These are used either singly or in combinations of two or more. Examples of the reaction solvent include n-pentane, iso-pentane, n-hexane, iso-hexane, 2,2-dimethyl-butane, n-heptane, iso-heptane, 2,2,4-trimethylpentane, n-octane, iso-octane, n-nonane, iso-nonane, its isomer, n-decane, n-pentadecane, cyclohexane, methylcyclohexane, dimethyl-cyclohexane, its isomer, and decalin as the saturated hydrocarbon; methyl acetate, ethyl acetate, butyl acetate, methyl propionate, n-methyl butyrate, n-ethyl butyrate, n-butyl butyrate, i-methyl butyrate, n-cyclohexyl butyrate, i-cyclohexyl butyrate, methyl valerate, and its isomer as the ester compound; and dimethyl ether, diethyl ether, di-n-propyl ether, di-iso-propyl ether, di-n-butyl ether, di-iso-butyl ether, di-sec-butyl ether, methyl propyl ether, ethyl propyl ether, methyl butyl ether, methyl pentyl ether, ethyl butyl ether, propyl butyl ether, methyl cyclopentyl ether, methyl cyclohexyl ether, ethyl cyclopentyl ether, ethyl cyclohexyl ether, propyl cyclopentyl ether, propyl cyclohexyl ether, butyl cyclopentyl ether, butyl cyclohexyl ether, ethylene glycol dimethyl ether, ethylene glycol diethyl ether, propylene glycol dimethyl ether, propylene glycol diethyl ether, diethylene glycol dimethyl ether, diethylene glycol diethyl ether, triethylene glycol dimethyl ether, triethylene glycol diethyl ether, tetrahydrofuran, methyl tetrahydrofuran, tetrahydropyran, methyl tetrahydropyran, 1,4-dioxane, dimethyl-1,4-dioxane, and their isomers as the ether compound.

The reaction system of the hydrogenation reduction in the present embodiment is formed from the compound (1), or a liquid phase containing the compound (1) and the reaction solvent, a gas phase of hydrogen gas, and a solid phase of the hydrogenation catalyst. As long as the reaction scheme is performed in a state where these coexist, the reaction system is not particularly limited. Conventionally known forms such as a tube type, a tank type, and a boiler type can be used as the type of a reaction vessel in the hydrogenation reduction of the present embodiment. A method for feeding a raw material composition may be any of a continuously feeding method and a batch method. Conventionally known methods such as a fixed bed, a fluid bed, and a suspension bed can be employed for the hydrogenation catalyst, and the hydrogenation catalyst is not particularly limited. In the case of the fixed bed flow method, the reaction can be performed under a trickle flow condition and a bubble flow condition. The raw material liquid may be fed in the gravity direction (downflow) or in the opposite direction (upflow). The raw material gas and the raw material liquid may be fed in either a parallel manner or a countercurrent manner.

A reaction temperature in the hydrogenation reduction of the present embodiment is preferably 50 to 350° C., more preferably 100 to 300° C., and still more preferably 150 to 280° C. When the reaction temperature is 50° C. or more, a higher hydrogenation rate is likely to be obtained. When the reaction temperature is 350° C. or less, the side reaction involving the decomposition of the raw material can be further suppressed, and the yield of the subject matter be further increased.

A reaction pressure in the hydrogenation reduction of the present embodiment is preferably 0.1 to 30 MPa, and more preferably 2 to 15 MPa. When the reaction pressure is 0.1 MPa or more, a higher hydrogenation rate is likely to be obtained, and the conversion of the compound (1) is improved. When the reaction pressure is 30 MPa or less, reaction facility cost can be suppressed lower, which is economically preferable.

The hydrogen gas used for the hydrogenation reduction of the present embodiment may not be particularly highly refined, and may have quality usually used for an industrial hydrogenation reaction. A higher purity of hydrogen gas to be used is preferable since the hydrogenation reaction is promoted depending on hydrogen partial pressure. However, the hydrogen gas may be mixed with gas inert to the reaction such as helium, argon, nitrogen, and methane. A ratio of the hydrogen gas to the compound (1) in the reaction system is preferably 0.1 to 300, and more preferably 0.5 to 100 when the ratio is represented as a feed molar ratio of the hydrogen gas to the compound (1) in the case of a batch reaction and as a mole supply speed ratio of the hydrogen gas to the compound (1) in the case of a feeding reaction. When the molar ratio of the hydrogen gas is 0.1 or more, the hydrogenation reaction is further promoted. When the molar ratio of the hydrogen gas is 300 or less, facility cost for cyclic use of excess hydrogen gas can be suppressed lower.

Next, the polyether diol of the present embodiment will be described in detail.

Although it is difficult to efficiently produce the polyether diol in the conventionally known method, some polyether diols including a single neo skeleton are known. On the other hand, a polyether diol including a plurality of neo skeletons is not known although the polyether diol has expected to have industrial advantages such as a low melting point provided by high asymmetry, and easy handling.

According to the present embodiment, more particularly, the producing method subjects the compound (1) produced from a precursor substance having different neo skeletons to hydrogenation reduction, and thereby a polyether diol including a plurality of neo skeletons can be easily and efficiently produced. A polyether diol capable of being produced by the present embodiment and including a plurality of neo skeletons is represented by the following general formula (A).

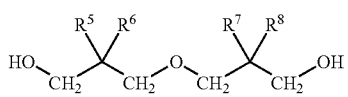

(A)

Herein, in the formula (A), $R^5$, $R^6$, $R^7$, and $R^8$ each independently represent a linear or branched alkyl group having 1 to 6 carbon atoms, and in each of $R^5$, $R^6$, $R^7$, and $R^8$, independently, one or two or more hydrogen atoms contained in the alkyl group may be replaced with an alkoxy group having 6 or less carbon atoms or a functional group inactive for a hydrogenation reduction reaction.

The compound represented by the general formula (A) is a polyether diol including different neo skeletons. Specifically, the compound is a polyether diol in which at least one of $R^5$ and $R^6$ is a different group from at least one of $R^7$ and $R^8$. At this time, $R^5$ and $R^6$ may be different groups, or $R^7$ and $R^8$ may be different groups. Furthermore, both $R^5$ and $R^6$ may be methyl groups, or both $R^7$ and $R^8$ may be methyl groups.

Another polyether diol capable of being produced by the present embodiment and including a plurality of neo skeletons is represented by the following general formulae (B1) and (B2).

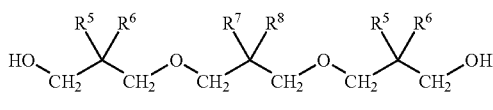

(B1)

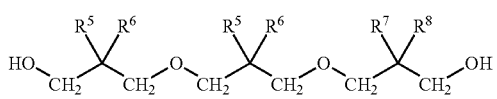

(B2)

Herein, in the formulae (B1) and (B2), $R^5$, $R^6$, $R^7$, and $R^8$ each independently represent a linear or branched alkyl group having 1 to 6 carbon atoms, and in each of $R^5$, $R^6$, $R^7$, and $R^8$, independently, one or two or more hydrogen atoms contained in the alkyl group may be replaced with an alkoxy group having 6 or less carbon atoms or a functional group inactive for a hydrogenation reduction reaction.

The compounds represented by the general formulae (B1) and (B2) are polyether diols including different neo skeletons. Specifically, the compound is a polyether diol in which at least one of $R^5$ and $R^6$ is a different group from at least one of $R^7$ and $R^8$. At this time, $R^5$ and $R^6$ may be different groups, or $R^7$ and $R^8$ may be different groups. Furthermore, both $R^5$ and $R^6$ may be methyl groups, or both $R^7$ and $R^8$ may be methyl groups.

Examples of the compound represented by the general formula (A) among the polyether diols of the present embodiment include compounds in which the combination of a group of $R^5$ and $R^6$ with a group of $R^7$ and $R^8$ is (a1)) to (a21) shown in the following Table.

| No. | $R^5$ and $R^6$ | $R^7$ and $R^8$ |
|---|---|---|
| a1 | $CH_3$ and $CH_3$ | $CH_3$ and $C_2H_5$ |
| a2 | $CH_3$ and $CH_3$ | $CH_3$ and $C_3H_7$ |
| a3 | $CH_3$ and $CH_3$ | $CH_3$ and $C_6H_{13}$ |
| a4 | $CH_3$ and $CH_3$ | $C_2H_5$ and $C_2H_5$ |
| a5 | $CH_3$ and $CH_3$ | $C_2H_5$ and $C_4H_9$ |
| a6 | $CH_3$ and $CH_3$ | $C_3H_7$ and $C_5H_{11}$ |
| a7 | $CH_3$ and $C_2H_5$ | $CH_3$ and $C_3H_7$ |
| a8 | $CH_3$ and $C_2H_5$ | $CH_3$ and $C_6H_{13}$ |
| a9 | $CH_3$ and $C_2H_5$ | $C_2H_5$ and $C_2H_5$ |
| a10 | $CH_3$ and $C_2H_5$ | $C_2H_5$ and $C_4H_9$ |
| a11 | $CH_3$ and $C_2H_5$ | $C_3H_7$ and $C_5H_{11}$ |
| a12 | $CH_3$ and $C_3H_7$ | $CH_3$ and $C_6H_{13}$ |
| a13 | $CH_3$ and $C_3H_7$ | $C_2H_5$ and $C_2H_5$ |
| a14 | $CH_3$ and $C_3H_7$ | $C_2H_5$ and $C_4H_9$ |
| a15 | $CH_3$ and $C_3H_7$ | $C_3H_7$ and $C_5H_{11}$ |
| a16 | $CH_3$ and $C_6H_{13}$ | $C_2H_5$ and $C_2H_5$ |
| a17 | $CH_3$ and $C_6H_{13}$ | $C_2H_5$ and $C_4H_9$ |
| a18 | $CH_3$ and $C_6H_{13}$ | $C_3H_7$ and $C_5H_{11}$ |
| a19 | $C_2H_5$ and $C_2H_5$ | $C_2H_5$ and $C_4H_9$ |
| a20 | $C_2H_5$ and $C_2H_5$ | $C_3H_7$ and $C_5H_{11}$ |
| a21 | $C_2H_5$ and $C_4H_9$ | $C_3H_7$ and $C_5H_{11}$ |

Preferable combinations of a group of $R^5$ and $R^6$ with a group of $R^7$ and $R^8$ among the compounds of the general formula (A) represented by the above Table are shown in the following Table.

| No. | $R^5$ and $R^6$ | $R^7$ and $R^8$ |
|---|---|---|
| a1 | $CH_3$ and $CH_3$ | $CH_3$ and $C_2H_5$ |
| a2 | $CH_3$ and $CH_3$ | $CH_3$ and $C_3H_7$ |
| a3 | $CH_3$ and $CH_3$ | $CH_3$ and $C_6H_{13}$ |
| a4 | $CH_3$ and $CH_3$ | $C_2H_5$ and $C_2H_5$ |
| a5 | $CH_3$ and $CH_3$ | $C_2H_5$ and $C_4H_9$ |
| a6 | $CH_3$ and $CH_3$ | $C_3H_7$ and $C_5H_{11}$ |
| a10 | $CH_3$ and $C_2H_5$ | $C_2H_5$ and $C_4H_9$ |
| a14 | $CH_3$ and $C_3H_7$ | $C_2H_5$ and $C_4H_9$ |
| a17 | $CH_3$ and $C_6H_{13}$ | $C_2H_5$ and $C_4H_9$ |
| a19 | $C_2H_5$ and $C_2H_5$ | $C_2H_5$ and $C_4H_9$ |
| a21 | $C_2H_5$ and $C_4H_9$ | $C_3H_7$ and $C_5H_{11}$ |

Particularly preferable combinations of a group of $R^5$ and $R^6$ with a group of $R^7$ and $R^8$ among the preferable compounds of the general formula (A) represented by the above Table are shown in the following Table.

| No. | $R^5$ and $R^6$ | $R^7$ and $R^8$ |
|---|---|---|
| a1 | $CH_3$ and $CH_3$ | $CH_3$ and $C_2H_5$ |
| a2 | $CH_3$ and $CH_3$ | $CH_3$ and $C_3H_7$ |
| a3 | $CH_3$ and $CH_3$ | $CH_3$ and $C_6H_{13}$ |
| a4 | $CH_3$ and $CH_3$ | $C_2H_5$ and $C_2H_5$ |
| a5 | $CH_3$ and $CH_3$ | $C_2H_5$ and $C_4H_9$ |
| a6 | $CH_3$ and $CH_3$ | $C_3H_7$ and $C_5H_{11}$ |

Examples of the compounds represented by the general formulae (B1) and (B2) among the polyether diols of the present embodiment include compounds in which the combination of a group of $R^5$ and $R^6$ with a group of $R^7$ and $R^8$ is (b1) to (b42) shown in the following Table.

| No. | $R^5$ and $R^6$ | $R^7$ and $R^8$ |
|---|---|---|
| b1 | $CH_3$ and $CH_3$ | $CH_3$ and $C_2H_5$ |
| b2 | $CH_3$ and $CH_3$ | $CH_3$ and $C_3H_7$ |
| b3 | $CH_3$ and $CH_3$ | $CH_3$ and $C_6H_{13}$ |
| b4 | $CH_3$ and $CH_3$ | $C_2H_5$ and $C_2H_5$ |
| b5 | $CH_3$ and $CH_3$ | $C_2H_5$ and $C_4H_9$ |
| b6 | $CH_3$ and $CH_3$ | $C_3H_7$ and $C_5H_{11}$ |

-continued

| No. | $R^5$ and $R^6$ | $R^7$ and $R^8$ |
|---|---|---|
| b7 | $CH_3$ and $C_2H_5$ | $CH_3$ and $CH_3$ |
| b8 | $CH_3$ and $C_2H_5$ | $CH_3$ and $C_3H_7$ |
| b9 | $CH_3$ and $C_2H_5$ | $CH_3$ and $C_6H_{13}$ |
| b10 | $CH_3$ and $C_2H_5$ | $C_2H_5$ and $C_2H_5$ |
| b11 | $CH_3$ and $C_2H_5$ | $C_2H_5$ and $C_4H_9$ |
| b12 | $CH_3$ and $C_2H_5$ | $C_3H_7$ and $C_5H_{11}$ |
| b13 | $CH_3$ and $C_3H_7$ | $CH_3$ and $CH_3$ |
| b14 | $CH_3$ and $C_3H_7$ | $CH_3$ and $C_2H_5$ |
| b15 | $CH_3$ and $C_3H_7$ | $CH_3$ and $C_6H_{13}$ |
| b16 | $CH_3$ and $C_3H_7$ | $C_2H_5$ and $C_2H_5$ |
| b17 | $CH_3$ and $C_3H_7$ | $C_2H_5$ and $C_4H_9$ |
| b18 | $CH_3$ and $C_3H_7$ | $C_3H_7$ and $C_5H_{11}$ |
| b19 | $CH_3$ and $C_6H_{13}$ | $CH_3$ and $CH_3$ |
| b20 | $CH_3$ and $C_6H_{13}$ | $CH_3$ and $C_2H_5$ |
| b21 | $CH_3$ and $C_6H_{13}$ | $CH_3$ and $C_3H_7$ |
| b22 | $CH_3$ and $C_6H_{13}$ | $C_2H_5$ and $C_2H_5$ |
| b23 | $CH_3$ and $C_6H_{13}$ | $C_2H_5$ and $C_4H_9$ |
| b24 | $CH_3$ and $C_6H_{13}$ | $C_3H_7$ and $C_5H_{11}$ |
| b25 | $C_2H_5$ and $C_2H_5$ | $CH_3$ and $CH_3$ |
| b26 | $C_2H_5$ and $C_2H_5$ | $CH_3$ and $C_2H_5$ |
| b27 | $C_2H_5$ and $C_2H_5$ | $CH_3$ and $C_3H_7$ |
| b28 | $C_2H_5$ and $C_2H_5$ | $CH_3$ and $C_6H_{13}$ |
| b29 | $C_2H_5$ and $C_2H_5$ | $C_2H_5$ and $C_4H_9$ |
| b30 | $C_2H_5$ and $C_2H_5$ | $C_3H_7$ and $C_5H_{11}$ |
| b31 | $C_2H_5$ and $C_4H_9$ | $CH_3$ and $CH_3$ |
| b32 | $C_2H_5$ and $C_4H_9$ | $CH_3$ and $C_2H_5$ |
| b33 | $C_2H_5$ and $C_4H_9$ | $CH_3$ and $C_3H_7$ |
| b34 | $C_2H_5$ and $C_4H_9$ | $CH_3$ and $C_6H_{13}$ |
| b35 | $C_2H_5$ and $C_4H_9$ | $C_2H_5$ and $C_2H_5$ |
| b36 | $C_2H_5$ and $C_4H_9$ | $C_3H_7$ and $C_5H_{11}$ |
| b37 | $C_3H_7$ and $C_5H_{11}$ | $CH_3$ and $CH_3$ |
| b38 | $C_3H_7$ and $C_5H_{11}$ | $CH_3$ and $C_2H_5$ |
| b39 | $C_3H_7$ and $C_5H_{11}$ | $CH_3$ and $C_3H_7$ |
| b40 | $C_3H_7$ and $C_5H_{11}$ | $CH_3$ and $C_6H_{13}$ |
| b41 | $C_3H_7$ and $C_5H_{11}$ | $C_2H_5$ and $C_2H_5$ |
| b42 | $C_3H_7$ and $C_5H_{11}$ | $C_2H_5$ and $C_4H_9$ |

Preferable combinations of a group of $R^5$ and $R^6$ with a group of $R^7$ and $R^8$ among the compounds of the general formulae (B1) and (B2) represented by the above Table are shown in the following Table.

| No. | $R^5$ and $R^6$ | $R^7$ and $R^8$ |
|---|---|---|
| b1 | $CH_3$ and $CH_3$ | $CH_3$ and $C_2H_5$ |
| b2 | $CH_3$ and $CH_3$ | $CH_3$ and $C_3H_7$ |
| b3 | $CH_3$ and $CH_3$ | $CH_3$ and $C_6H_{13}$ |
| b4 | $CH_3$ and $CH_3$ | $C_2H_5$ and $C_2H_5$ |
| b5 | $CH_3$ and $CH_3$ | $C_2H_5$ and $C_4H_9$ |
| b6 | $CH_3$ and $CH_3$ | $C_3H_7$ and $C_5H_{11}$ |
| b7 | $CH_3$ and $C_2H_5$ | $CH_3$ and $CH_3$ |
| b11 | $CH_3$ and $C_2H_5$ | $C_2H_5$ and $C_4H_9$ |
| b13 | $CH_3$ and $C_3H_7$ | $CH_3$ and $CH_3$ |
| b17 | $CH_3$ and $C_3H_7$ | $C_2H_5$ and $C_4H_9$ |
| b19 | $CH_3$ and $C_6H_{13}$ | $CH_3$ and $CH_3$ |
| b23 | $CH_3$ and $C_6H_{13}$ | $C_2H_5$ and $C_4H_9$ |
| b25 | $C_2H_5$ and $C_2H_5$ | $CH_3$ and $CH_3$ |
| b29 | $C_2H_5$ and $C_2H_5$ | $C_2H_5$ and $C_4H_9$ |
| b31 | $C_2H_5$ and $C_4H_9$ | $CH_3$ and $CH_3$ |
| b32 | $C_2H_5$ and $C_4H_9$ | $CH_3$ and $C_2H_5$ |
| b33 | $C_2H_5$ and $C_4H_9$ | $CH_3$ and $C_3H_7$ |
| b34 | $C_2H_5$ and $C_4H_9$ | $CH_3$ and $C_6H_{13}$ |
| b35 | $C_2H_5$ and $C_4H_9$ | $C_2H_5$ and $C_2H_5$ |
| b36 | $C_2H_5$ and $C_4H_9$ | $C_3H_7$ and $C_5H_{11}$ |
| b37 | $C_3H_7$ and $C_5H_{11}$ | $CH_3$ and $CH_3$ |
| b42 | $C_3H_7$ and $C_5H_{11}$ | $C_2H_5$ and $C_4H_9$ |

Particularly preferable combinations of a group of $R^5$ and $R^6$ with a group of $R^7$ and $R^8$ among the preferable compounds of the formulae (B1) and (B2) represented by the above Table are shown in the following Table.

| No. | $R^5$ and $R^6$ | $R^7$ and $R^8$ |
|---|---|---|
| b1 | $CH_3$ and $CH_3$ | $CH_3$ and $C_2H_5$ |
| b2 | $CH_3$ and $CH_3$ | $CH_3$ and $C_3H_7$ |
| b3 | $CH_3$ and $CH_3$ | $CH_3$ and $C_6H_{13}$ |
| b4 | $CH_3$ and $CH_3$ | $C_2H_5$ and $C_2H_5$ |
| b5 | $CH_3$ and $CH_3$ | $C_2H_5$ and $C_4H_9$ |
| b6 | $CH_3$ and $CH_3$ | $C_3H_7$ and $C_5H_{11}$ |
| b7 | $CH_3$ and $C_2H_5$ | $CH_3$ and $CH_3$ |
| b13 | $CH_3$ and $C_3H_7$ | $CH_3$ and $CH_3$ |
| b19 | $CH_3$ and $C_6H_{13}$ | $CH_3$ and $CH_3$ |
| b25 | $C_2H_5$ and $C_2H_5$ | $CH_3$ and $CH_3$ |
| b31 | $C_2H_5$ and $C_4H_9$ | $CH_3$ and $CH_3$ |
| b37 | $C_3H_7$ and $C_5H_{11}$ | $CH_3$ and $CH_3$ |

A polyether diol represented by the general formulae (A), (B1), and (B2) and including a plurality of neo skeletons is a novel substance.

EXAMPLES

Hereinafter, the producing method of the present invention will be more specifically described with reference to Examples and Comparative Examples. However, the present invention is not limited to those Examples as long as others do not deviate from the gist of the present invention.

Reaction results of hydrogenation reduction were evaluated on the basis of the number of moles of quaternary carbon (neo skeleton) in feed raw materials, raw materials in a reaction liquid, and a generated polyether diol.

conversion (%) of raw material acetal (compound (1))=100×[1−(the number of moles of raw material quaternary carbon remaining in reaction liquid)/(the number of moles of quaternary carbon in feed raw material)]

selectivity (%) of each generated polyether diol=100×(the number of moles of quaternary carbon in desired product material)/[(the number of moles of quaternary carbon in feed raw material)−(the number of moles of raw material quaternary carbon remaining in reaction liquid)]

When isomers were present in the compound (1), a value obtained by combining the isomers was used. The generated polyether diols were classified for every number of the quaternary carbons in a molecule, combined, and expressed as selectivities of a compound (2) and a compound (3).

The isolated compounds were identified by $^1$H-NMR and $^{13}$C-NMR measurements. Measurement conditions will be shown below.

device: ECA500 (1H-single pulse, 13C-single pulse) (trade name) manufactured by JEOL Ltd.
1H-NMR
nuclide: $^1$H
measurement frequency: 500 MHz
cumulated number: 16 times
measurement sample: 5% $CDCl_3$ solution
$^{13}$C-NMR
nuclide: $^{13}$C
measurement frequency: 125 MHz
cumulated number: 512 times
measurement sample: 5% $CDCl_3$ solution The compounds which were not isolated were identified by specifying molecular structures of the compounds by GC-MS measurement of reaction liquids obtained in Examples (a chemical ionization method [CI+], high-resolution mass spectrometry [milli-mass]). Measurement conditions will be shown below.

devices: Agilent 7890A (trade name) manufactured by Agilent Technologies, Inc. and ACCU-TOF-GCV (JMS-T100GCV) (trade name) (model number name) manufactured by JEOL Ltd.

GC Measurement Condition capillary: HP-5 (length of 30 m×inner diameter of 0.32 mm, 0.25 μm) (trade name) manufactured by Agilent Technologies, Inc.

column condition: a temperature was increased to 300° C. from 80° C. at 10° C./min, and then held.

carrier: He, split ratio: 1/20

MS measurement condition: chemical ionization method, detector condition: ionization voltage: 200 eV, ionizing current: 300 μA, detector voltage: 1700 V The following materials were used to isolate the product material by a chromatographic method.

filler: "Wakogel C-200" (trade name) manufactured by Wako Pure Chemical Industries, Ltd.

developing solvent: ethyl acetate-toluene

The compound (1) (cyclic acetal compound) which was a reaction raw material was prepared by the following method.

Raw Material Preparation Example 1

Preparation of 2-(5,5-Dimethyl-[1,3]dioxane-2-yl)-2-methyl-propane-1-ol 131.3 g of 2,2-dimethyl-3-hydroxy-propionaldehyde (hydroxypivalaldehyde, manufactured by Mitsubishi Gas Chemical Company, Inc., purity: 99.8%), 136.0 g of 2,2-dimethyl-1,3-propanediol (neopentyl glycol (reagent) manufactured by Tokyo Chemical Industry Co., Ltd.), 705 g of benzene, and 3.0 g of granular Nafion ("NR-50" (trade name) manufactured by Sigma-Aldrich Corporation) were placed in a 2 L round bottom flask. Water generated under normal pressure was extracted out of a system using a Dean-Stark trap by an azeotrope together with benzene, and the reaction was performed until the distillation of the water stopped. This was filtered, and then recrystallized by condensing and cooling, to obtain a crystal of 2-(5,5-dimethyl-[1,3]dioxane-2-yl)-2-methyl-propane-1-ol. This synthetic reaction scheme will be shown below.

Synthetic Reaction of Compound (1) of Raw Material Preparation Example 1

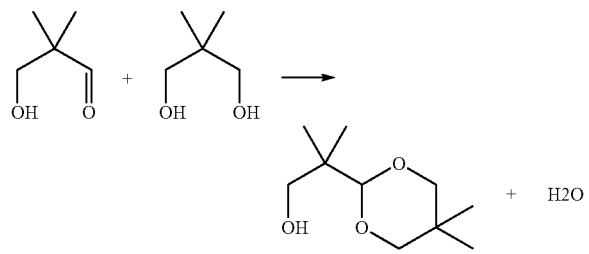

Raw Material Preparation Example 2

Preparation of 2-(5,5-Diethyl-[1,3]dioxane-2-yl)-2-methyl-propane-1-ol

A crystal of 2-(5,5-diethyl-[1,3]dioxane-2-yl)-2-methyl-propane-1-ol was obtained in the same manner as in raw material preparation example 1 except that 77.6 g of 2,2-dimethyl-3-hydroxy-propionaldehyde (hydroxypivalaldehyde, manufactured by Mitsubishi Gas Chemical Company, Inc., purity: 99.8%) was used in place of 131.3 g of 2,2-dimethyl-3-hydroxy-propionaldehyde, and 91.3 g of 2,2-diethyl-1,3-propanediol (reagent manufactured by Tokyo Chemical Industry Co., Ltd.) was used in place of 136.0 g of 2,2-dimethyl-1,3-propanediol. This synthetic reaction scheme will be shown below.

Synthetic Reaction of Compound (1) of Raw Material Preparation Example 2

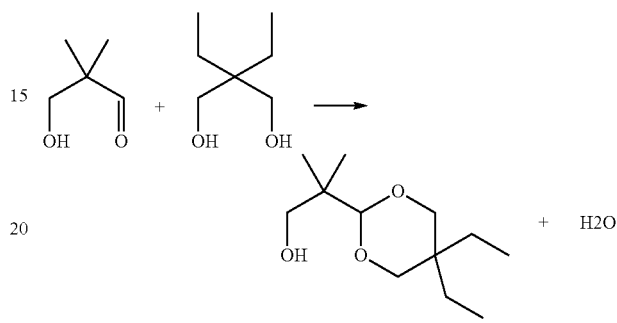

Raw Material Preparation Example 3

Preparation of 2-(5-Butyl-5-ethyl-[1,3]dioxane-2-yl)-2-methyl-propane-1-ol

A crude 2-(5-butyl-5-ethyl-[1,3]dioxane-2-yl)-2-methyl-propane-1-ol/benzene solution was obtained in the same reaction as in raw material preparation example 1 except that 73.6 g of 2,2-dimethyl-3-hydroxy-propionaldehyde (hydroxypivalaldehyde, manufactured by Mitsubishi Gas Chemical Company, Inc., purity: 99.8%) was used in place of 131.3 g of 2,2-dimethyl-3-hydroxy-propionaldehyde, and 111.8 g of 2-butyl-2-ethyl-1,3-propanediol (reagent manufactured by Tokyo Chemical Industry Co., Ltd.) was used in place of 136.0 g of 2,2-dimethyl-1,3-propanediol. Benzene was distilled away out of the reaction liquid, and 2-(5-butyl-5-ethyl-[1,3]dioxane-2-yl)-2-methyl-propane-1-ol (99.4% as purity in GC when the isomers were combined) was then obtained by distillation under reduced pressure.

Raw Material Preparation Example 4

Preparation of 2-(5-Propyl-5-methyl-[1,3]dioxane-2-yl)-2-methyl-propane-1-ol

A crude 2-(5-propyl-5-methyl-[1,3]dioxane-2-yl)-2-methyl-propane-1-ol/benzene solution was obtained in the same reaction as in raw material preparation example 1 except that 73.0 g of 2,2-dimethyl-3-hydroxy-propionaldehyde (hydroxypivalaldehyde, manufactured by Mitsubishi Gas Chemical Company, Inc., purity: 99.8%) was used in place of 131.3 g of 2,2-dimethyl-3-hydroxy-propionaldehyde, and 92.5 g of 2-propyl-2-methyl-1,3-propanediol (reagent manufactured by Tokyo Chemical Industry Co., Ltd.) was used in place of 136.0 g of 2,2-dimethyl-1,3-propanediol. Benzene was distilled away out of the reaction liquid, and 2-(5-propyl-5-methyl-[1,3]dioxane-2-yl)-2-methyl-propane-1-ol (99.2% as purity in GC when the isomers were combined) was then obtained by distillation under reduced pressure.

Reference Raw Material Preparation Example 1

Preparation of 2-([1,3]Dioxane-2-yl)-2-methyl-propane-1-ol

A crude 2-([1,3]dioxane-2-yl)-2-methyl-propane-1-ol/benzene solution was obtained in the same reaction as in raw material preparation example 1 except that 77.1 g of 2,2-dimethyl-3-hydroxy-propionaldehyde (hydroxypivalaldehyde, manufactured by Mitsubishi Gas Chemical Company, Inc., purity: 99.8%) was used in place of 131.3 g of 2,2-dimethyl-3-hydroxy-propionaldehyde, and 64.0 g of 1,3-propanediol (reagent manufactured by Tokyo Chemical Industry Co., Ltd.) was used in place of 136.0 g of 2,2-dimethyl-1,3-propanediol. Benzene was distilled away out of the reaction liquid, and 2-([1,3]dioxane-2-yl)-2-methyl-propane-1-ol (99.0% as purity in GC) was then obtained by distillation under reduced pressure. This synthetic reaction scheme will be shown below.

Synthetic Reaction of Compound (1) of Reference Raw Material Preparation Example 1

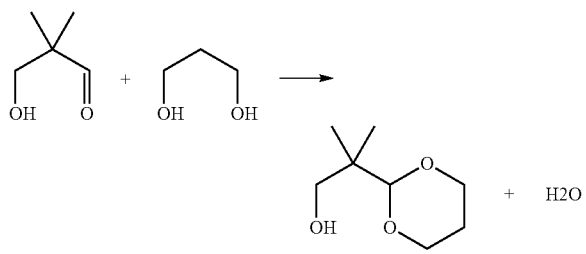

Reference Raw Material Preparation Example 2

Preparation of 2-(5-Methyl-[1,3]dioxane-2-yl)-2-methyl-propane-1-ol

A crude 2-(5-methyl-[1,3]dioxane-2-yl)-2-methyl-propane-1-ol/benzene solution was obtained in the same reaction as in raw material preparation example 1 except that 69.1 g of 2,2-dimethyl-3-hydroxy-propionaldehyde (hydroxypivalaldehyde, manufactured by Mitsubishi Gas Chemical Company, Inc., purity: 99.8%) was used in place of 131.3 g of 2,2-dimethyl-3-hydroxy-propionaldehyde, and 64.1 g of 2-methyl-1,3-propanediol (reagent manufactured by Tokyo Chemical Industry Co., Ltd.) was used in place of 136.0 g of 2,2-dimethyl-1,3-propanediol. Benzene was distilled away out of the reaction liquid, and 2-(5-methyl-[1,3]dioxane-2-yl)-2-methyl-propane-1-ol (99.2% as purity in GC when the isomers were combined) was then obtained by distillation under reduced pressure. This synthetic reaction scheme will be shown below.

Synthetic Reaction of Compound (1) of Reference Raw Material Preparation Example 2

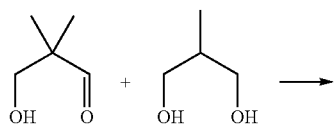

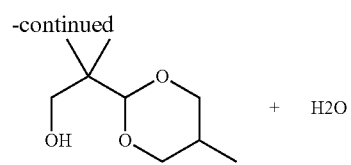

Carrier Preparation Example 1

Zirconium oxide used as a carrier for a metal component was prepared by the following method.

A white precipitation was obtained by dropping 15.5 g of 28% ammonia water to 505 g of a zirconium oxynitrate aqueous solution having a concentration of 25% by mass in terms of the zirconium oxide ($ZrO_2$) under stirring. This was filtered, and washed with ion-exchange water, followed by drying at 110° C. for 10 hours, to obtain hydrous zirconium oxide. This was placed in a porcelain crucible, and fired at 400° C. for 3 hours in air using an electric furnace. Then, the obtained fired product was ground in an agate mortar to obtain powdered zirconium oxide (hereinafter, represented as a "carrier A"). The BET specific surface area of the carrier A (measured by a nitrogen adsorption method, hereinafter the same applies) was 102.7 $m^2/g$.

Carrier Preparation Example 2

An apatite compound used as a carrier for a metal component was prepared by the following method.

78.7 g of calcium nitrate tetrahydrate was dissolved in 300.5 g of ion-exchange water, and 260 mL of 28% ammonia water was added thereto. 26.4 g of diammonium hydrogen phosphate was dissolved in 500.6 g of ion-exchange water, and 150 mL of 28% ammonia water and 150 mL of ion-exchange water were added thereto. When the diammonium hydrogen phosphate-ammonia solution was added little by little to the calcium nitrate-ammonia solution under stirring, the obtained solution became cloudy gradually to obtain a white precipitation. After the end of addition, the solution was left after being stirred for about 2 hours. Then, the left precipitation was filtered and washed with ion-exchange water, followed by drying at 110° C. for 10 hours. Then, the dried product was fired at 500° C. for 3 hours in air using an electric furnace. Then, the fired product was ground in an agate mortar to obtain powdered apatite hydroxide (hereinafter, represented as a "carrier B"). The BET specific surface area of the carrier B was 60.7 $m^2/g$.

Catalyst Preparation Example 1

A catalyst containing palladium as a specific metal component was prepared by the following method.

A 0.66% by mass palladium chloride-0.44% by mass sodium chloride aqueous solution was added to 5.0 g of a carrier A, to allow the metal component to be adsorbed on the carrier. Then, a formaldehyde-sodium hydroxide aqueous solution was poured onto the carrier A to quickly reduce the adsorbed metal component. Then, the catalyst was washed with ion-exchange water and dried to prepare a 1.0% by mass palladium-supported zirconium oxide catalyst (hereinafter, represented as an "A1 catalyst").

Catalyst Preparation Example 2

A 2.0% by mass palladium-supported zirconium oxide catalyst (hereinafter, represented as an "A2 catalyst") was prepared in the same manner as in the catalyst preparation example 1 except that an amount of palladium to be supported was changed.

Catalyst Preparation Example 3

A formed catalyst containing palladium as a specific metal component was prepared by the following method.

Only the A1 catalyst obtained in the catalyst preparation example 1 was subjected to tablet forming without adding a forming auxiliary agent or the like, crushed, and then sieved to 0.5 to 1.4 mm, to obtain a granular 1.0% by mass palladium-supported zirconium oxide catalyst (hereinafter, represented as an "A3 catalyst").

Catalyst Preparation Example 4

A catalyst containing palladium as a specific metal component was prepared by the following method.

A 0.32% by mass palladium acetate-acetone solution was added to 5.0 g of a carrier B, to be adsorbed. Then, palladium acetate was supported on the carrier by evaporating acetone to dryness. This was placed in a porcelain crucible, and fired at 400° C. for 3 hours in air using an electric furnace. The fired product was reduced at 110° C. under a hydrogen gas air current, to prepare a 1.0% by mass palladium-supported apatite catalyst (hereinafter, represented as a "B1 catalyst").

Catalyst Preparation Example 5

3.0 g of a B1 catalyst was added to a 5.9% by mass sodium chloride aqueous solution, and these were stirred for 2 hours, to perform ion exchange treatment. Then, the catalyst was filtration-washed with ion-exchange water, followed by drying, to prepare a 1.0% by mass palladium-supported catalyst (hereinafter, represented as a "B2 catalyst") of an apatite hydroxide carrier partially ion-exchanged to a chloride. As a result of elemental analysis by ICP emission analysis, the catalyst contained chlorine equivalent to about 5% of all hydroxyl groups.

Catalyst Preparation Example 6

A catalyst containing nickel as a specific metal component was prepared by the following method.

305.0 g of nickel nitrate hexahydrate was dissolved in 840 g of ion-exchange water at 40° C., to prepare a nickel metal salt aqueous solution. 190.6 g of ammonium hydrogen carbonate was dissolved in 2.4 kg of ion-exchange water under sufficient stirring while raising the temperature to 40° C. To the ammonium hydrogen carbonate aqueous solution, the nickel metal salt aqueous solution held at 40° C. was added under sufficient stirring to prepare a precipitation slurry of nickel carbonate. Aside from the preparation, 118.4 g of a 25% by mass zirconium oxynitrate aqueous solution in terms of zirconium oxide ($ZrO_2$) was mixed with 300 g of ion-exchange water, to prepare a zirconium nitrate aqueous solution. 42.8 g of ammonium hydrogen carbonate was dissolved in 530 g of ion-exchange water, to prepare an ammonium hydrogen carbonate aqueous solution. The zirconium nitrate aqueous solution and the ammonium hydrogen carbonate aqueous solution were simultaneously poured to the precipitation slurry of nickel carbonate previously prepared, under stirring, to precipitate zirconium carbonate. The precipitation slurry thus obtained was stirred for 30 minutes while being held at 40° C. Then, the precipitation slurry was filtered and washed, to obtain a precipitation. The precipitation was dried at 110° C. overnight and then fired at 380° C. for 18 hours in an air atmosphere, to prepare a powdered nickel-zirconium oxide catalyst (hereinafter, represented as a "Ni-1 catalyst"). This catalyst was activated by reducing at 400° C. under a hydrogen gas air current.

Catalyst Preparation Example 7

A catalyst containing copper as a specific metal component was prepared by the following method.

550 g of a 25% by mass zirconium oxynitrate aqueous solution in terms of zirconium oxide ($ZrO_2$) was dissolved in 2.5 L of ion-exchange water, and the obtained solution was held at 40° C. 197.5 g of ammonium hydrogen carbonate was dissolved in 5 L of ion-exchange water, and the obtained solution was heated to 40° C. To the solution, the zirconium oxynitrate aqueous solution was poured under stirring, and the obtained solution was held for 30 minutes at 40° C. Then, filtering and washing were performed to obtain about 830 g of a cake derived from zirconium oxide. Aside from the preparation, 570 g of copper nitrate trihydrate was dissolved in 4.4 L of ion-exchange water, and the obtained solution was held at 40° C. 283 g of anhydrous sodium carbonate was dissolved in 3.5 L of ion-exchange water, and the obtained solution was heated to 40° C. To the solution, the copper nitrate aqueous solution was poured under stirring, to obtain about 550 g of a copper-containing cake. 500 g of the copper-containing cake thus obtained and 390 g of the cake derived from zirconium oxide were placed in a grinder and kneaded, to obtain a paste. The paste was dried at 80° C., and then fired at 380° C. for 2 hours, to prepare a powdered copper-zirconium oxide catalyst (hereinafter, represented as a "Cu-1 catalyst"). This catalyst was activated by reducing at 170° C. under a nitrogen-hydrogen mixed gas air current.

A hydrogenation reduction reaction was carried out by the following method.

Example 1

0.60 g of an A1 catalyst, 2.40 g of 2-(5,5-dimethyl-[1,3] dioxane-2-yl)-2-methyl-propane-1-ol of raw material preparation example 1, and 24.0 g of diisopropylether were placed in a 100 mL SUS reactor vessel, and the reactor vessel was purged with nitrogen gas. Then, the reactor vessel was filled with hydrogen gas at 8.5 MPa. The temperature was increased to a reaction temperature of 230° C. for the reaction for 2 hours. Then, the reactor vessel was cooled. The contents in the reactor vessel were sampled, and gas-chromatographically analyzed.

As a result, the conversion of a compound (1) was 95.8%. The selectivity of 3-(3-hydroxy-2,2-dimethyl-propoxy)-2,2-dimethyl-propane-1-ol (hereinafter, represented as a "compound MMMM") of a compound (2) was 89.6%; the selectivity of 3-[3-(3-hydroxy-2,2-dimethyl-propoxy)-2,2-dimethyl-propoxy]-2,2-dimethyl-propane-1-ol (hereinafter, represented as a "compound MMMMMM") of a compound (3) was 4.2%; and the total of both the selectivities was 93.8%.

The product materials were identified by the following method.

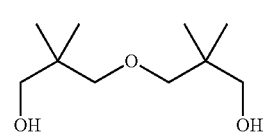

(Compound MMMM)

The obtained reaction liquid was filtered to separate the catalyst. Then, the reaction liquid was recrystallized to obtain a product material. The structure of the product material was confirmed by subjecting the product material to NMR analysis.

$^1$H NMR (500 MHz, CDCl$_3$) δ 0.91 (3H×4, 2s, Me$_2$C×2), 2.50-2.68 (2H, bs, OH×2), 3.26 (4H, s, —CH$_2$—O—×2), 3.43 (4H, s, —C$\underline{H}_2$OH×2); $^{13}$C NMR (125 MHz, CDCl$_3$) δ 21.8, 36.4, 70.8, 79.7.

(Compound MMMMMM)

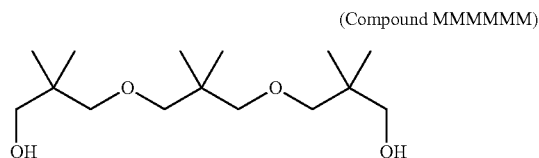 [SMILES: CC(C)(CO)COCC(C)(C)COCC(C)(C)CO]

The obtained reaction liquid was subjected to chromatography to isolate a product material. The structure of the product material was confirmed by subjecting the product material to NMR analysis.

$^1$H NMR (500 MHz, CDCl$_3$) δ 0.89, 0.91 (3H×6, 2s, Me$_2$C×3), 3.16, 3.25 (4H×2, 2s, —CH$_2$—O—×4), 3.42 (4H, s, —C$\underline{H}_2$OH×2) 3.46 (2H, bs, OH×2); $^{13}$C NMR (125 MHz, CDCl$_3$) δ 21.8, 22.4, 36.0, 36.3, 71.5, 77.5, 80.1.

From these results, when a polyether diol having a ring-opening structure formed by adding one hydrogen molecule to the compound (1) was generated, the compound (3) in which a neo skeleton included in the generated compound (2) was further added to the compound (2) was also confirmed to be simultaneously generated. Hereinafter, a reaction scheme in Example 1 will be shown.

Example 1

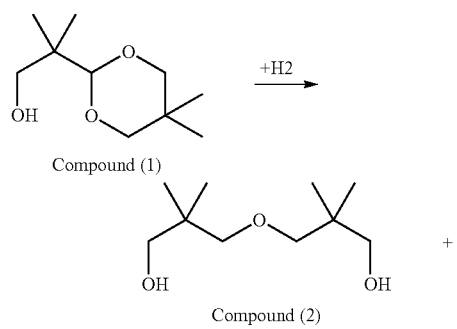

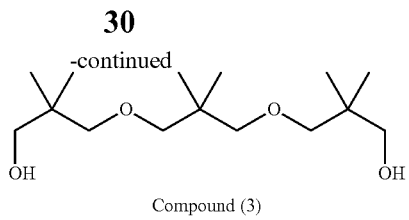

Compound (3)

Example 2

A reaction was performed in the same manner as in Example 1 except that an A1 catalyst was changed to an A2 catalyst. The conversion of a compound (1) was 98.9%. The selectivity of a compound MMMM of a compound (2) was 68.5%; the selectivity of a compound MMMMMM of a compound (3) was 13.5%; and the total of both the selectivities was 82.0%.

Examples 3 to 6

Reactions were performed in the same manner as in Example 2 except that reaction solvents and reaction conditions were changed. Catalysts, reaction solvents, reaction conditions, and reaction results are shown in Table 1.

TABLE 1

|  | Example 3 | Example 4 | Example 5 | Example 6 |
| --- | --- | --- | --- | --- |
| Catalyst name | A2 catalyst | | | |
| Reaction temperature | 230° C. | 230° C. | 230° C. | 210° C. |
| Reaction time | 2.0 hr | 2.5 hr | 3.5 hr | 2.5 hr |
| Reaction solvent | ethyl ether | n-butyl ether | 1,4-dioxane | n-hexane |
| Conversion of compound (1) | 98.6% | 90.1% | 98.0% | 83.9% |
| Selectivity of compound (2) | 63.3% | 79.4% | 91.3% | 85.1% |
| Selectivity of compound (3) | 15.3% | 7.0% | 2.8% | 3.1% |
| Selectivity of compounds (2) + (3) | 78.6% | 86.4% | 94.1% | 88.2% |

Examples 7 to 11

Reactions were performed in the same manner as in Example 1 except that kinds and amounts to be fed of a compound (1), reaction solvents, and reaction times were changed. Catalysts, reaction solvents, reaction conditions, reaction raw material feed masses, and reaction results are shown in Table 2.

TABLE 2

|  | Example 7 | Example 8 | Example 9 | Example 10 | Example 11 |
| --- | --- | --- | --- | --- | --- |
| Catalyst name | A1 catalyst | | | | |
| Reaction temperature | 230° C. | 230° C. | 230° C. | 230° C. | 230° C. |
| Reaction time | 3.5 hr | 4.0 hr | 5.0 hr | 2.0 hr | 5.0 hr |
| Reaction raw material feed mass | Raw material preparation example 2 2.76 g | Raw material preparation example 3 2.84 g | Raw material preparation example 3 4.56 g | Raw material preparation example 4 2.92 g | Raw material preparation example 4 4.60 g |
| Reaction solvent | i-propyl ether | i-propyl ether | 1,4-dioxane | i-propyl ether | 1,4-dioxane |
| Conversion of compound (1) | 87.9% | 98.7% | 99.1% | 90.6% | 99.0% |
| Selectivity of compound (2) | 87.4% | 83.9% | 85.7% | 87.0% | 89.3% |

TABLE 2-continued

|  | Example 7 | Example 8 | Example 9 | Example 10 | Example 11 |
|---|---|---|---|---|---|
| Selectivity of compound (3) | 2.3% | 3.3% | 2.1% | 3.6% | 1.5% |
| Selectivity of compounds (2) + (3) | 89.7% | 87.2% | 87.8% | 90.6% | 90.8% |

In Example 7, 2-ethyl-2-(3-hydroxy-2,2-dimethyl-propoxymethyl)-butane-1-ol (hereinafter, represented as a "compound MMEE") was generated as a compound (2). 3-[2-Ethyl-2-(3-hydroxy-2,2-dimethyl-propoxymethyl)-butoxy]-2,2-dimethyl-propane-1-ol (hereinafter, represented as a "compound MMEEMM") and 2-ethyl-2-[3-(3-hydroxy-2,2-dimethyl-propoxy)-2,2-dimethyl-propoxymethyl]-butane-1-ol (hereinafter, represented as a "compound MMMMEE") were mainly generated as a compound (3).

The product materials were identified by the following method.

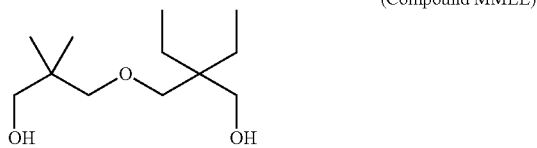
(Compound MMEE)

The obtained reaction liquid was filtered to separate the catalyst. Then, the reaction liquid was isolated by distillation to obtain a product material. The structure of the product material was confirmed by subjecting the product material to NMR analysis.

$^1$H NMR (500 MHz, CDCl$_3$) δ 0.81 (3H×2, 2t, C$\underline{H_3}$CH$_2$—×2), 0.90 (3H×2, 2s, Me$_2$C×2), 1.29 (2H×2, 2q, CH$_3$C$\underline{H_2}$C), 2.62-2.80 (2H, bs, OH×2), 3.24, 3.30 (2H×2, 2s, —CH$_2$—O—×2), 3.41, 3.47 (2H×2, 2s, —C$\underline{H_2}$OH×2); $^{13}$C NMR (125 MHz, CDCl$_3$) δ 7.22, 21.8, 22.9, 36.3, 41.0, 67.4, 70.5, 76.6, 79.4.

The melting point of the compound MMEE obtained by differential thermal analysis was 30° C. This is lower than the melting point (125° C.) of 2,2-dimethyl-1,3-propanediol and the melting point (61° C.) of 2,2-ethyl-1,3-propanediol. This is lower than the melting point (85° C.) of di-neopentyl glycol having a similar structure and excellent symmetry.

When the compound (1) which is the raw material of the present invention is subjected to hydrogenation reduction as in Example 1, the polyether diol (compound (2)) having the ring-opening structure formed by adding one hydrogen molecule is generated, and the compound (3) in which a neo skeleton included in the compound (2) generated herein is further added to the compound (2) is also simultaneously generated.

However, since the neo skeleton included in the compound MMEE has two different structures of 2,2-dimethyl-1,3-propanediol and 2,2-diethyl-1,3-propanediol in Example 7, the structure of the generated compound (3) is changed depending on the structure to be added. Since the compound MMEE has an asymmetrical structure, the structure of the generated compound (3) is also changed by the addition direction. Also in GC analysis of the actual reaction liquid, four compounds (hereinafter, represented as a "compound MMEEMM," a "compound MMMMEE," a "compound MMEEEE," and a "compound EEMMEE") were detected. In these identifications, there was used GC-MS measurement (a chemical ionization method [CI+], high-resolution mass spectrometry [milli-mass]) of the reaction liquid.

Since most molecules are ionized without fragmenting the molecules in the mass spectrometry of the chemical ionization method to perform mass spectrometry, information of a molecular weight can be obtained, and a composition formula can be simultaneously verified by performing the high-resolution mass spectrometry. The structure fragment in the molecule can be verified by similarly analyzing the spectrum of the fragment obtained by partial decomposition. The results of the compound MMEEMM, the compound MMMMEE, the compound MMEEEE, and the compound EEMMEE were obtained as shown in Table 3.

TABLE 3

|  | Actual measurement value (mu) | Estimated composition formula | Calculated mass (mu) | Mass difference (mu) |  |
|---|---|---|---|---|---|
| Compound MMEEMM | 305.26828 | $^{12}C_{17}{}^1H_{37}{}^{16}O_4$ | 305.26918 | −0.00090 | [M + H]$^+$ |
|  | 219.19691 | $^{12}C_{12}{}^1H_{27}{}^{16}O_3$ | 219.19602 | 0.00089 | [M − 85]$^+$ |
|  | 201.18696 | $^{12}C_{12}{}^1H_{25}{}^{16}O_2$ | 201.18545 | 0.00150 | [M − 103]$^+$ |
|  | 171.14094 | $^{12}C_{10}{}^1H_{19}{}^{16}O_2$ | 171.13850 | 0.00243 |  |
| Compound MMMMEE | 305.26837 | $^{12}C_{17}{}^1H_{37}{}^{16}O_4$ | 305.26918 | −0.00081 | [M + H]$^+$ |
|  | 219.19700 | $^{12}C_{17}{}^1H_{37}{}^{16}O_5$ | 219.19602 | 0.00098 |  |
|  | 201.18650 | $^{12}C_{17}{}^1H_{37}{}^{16}O_6$ | 201.18545 | 0.00104 |  |
|  | 191.16618 | $^{12}C_{10}{}^1H_{23}{}^{16}O_3$ | 191.16472 | 0.00146 | [M − 113]$^+$ |
|  | 173.15552 | $^{12}C_{10}{}^1H_{21}{}^{16}O_2$ | 173.15415 | 0.00137 | [M − 131]$^+$ |
| Compound MMEEEE | 333.29872 | $^{12}C_{19}{}^1H_{41}{}^{16}O_4$ | 333.30048 | −0.00176 | [M + H]$^+$ |
|  | 247.22807 | $^{12}C_{14}{}^1H_{31}{}^{16}O_3$ | 247.22732 | 0.00075 |  |
|  | 229.21791 | $^{12}C_{14}{}^1H_{29}{}^{16}O_2$ | 229.21675 | 0.00115 | [M − 103]$^+$ |
|  | 219.19662 | $^{12}C_{12}{}^1H_{27}{}^{16}O_3$ | 219.19602 | 0.00060 | [M − 113]$^+$ |
|  | 201.18650 | $^{12}C_{12}{}^1H_{25}{}^{16}O_2$ | 201.18545 | 0.00104 | [M − 131]$^+$ |
|  | 171.14009 | $^{12}C_{10}{}^1H_{19}{}^{16}O_2$ | 171.13850 | 0.00159 |  |
|  | 115.11395 | $^{12}C_7{}^1H_{15}{}^{16}O_1$ | 115.11229 | 0.00166 |  |

TABLE 3-continued

| | Actual measurement value (mu) | Estimated composition formula | Calculated mass (mu) | Mass difference (mu) | |
|---|---|---|---|---|---|
| Compound EEMMEE | 333.29878 | $^{12}C_{19}{}^{1}H_{41}{}^{16}O_{4}$ | 333.30048 | −0.00170 | $[M + H]^+$ |
| | 219.19704 | $^{12}C_{12}{}^{1}H_{27}{}^{16}O_{3}$ | 219.19602 | 0.00102 | $[M − 113]^+$ |
| | 201.18722 | $^{12}C_{12}{}^{1}H_{25}{}^{16}O_{2}$ | 201.18545 | 0.00177 | $[M − 131]^+$ |

From the mass number (molecular weight M+1) of $[M+H]^+$ protonated while the molecular structure is held, it is found that the compound MMEEMM and the compound MMMMEE have a composition formula $C_{17}H_{36}O_4$, i.e., have two 2,2-dimethyl-1,3-propanediol skeletons and a 2,2-diethyl-1,3-propanediol skeleton in the molecule; and these are connected by the ether bond. The compound MMEEMM and the compound MMMMEE are considered to be isomers in which the arrangement of substituted 1,3-propanediol skeletons is different.

Figure 2:
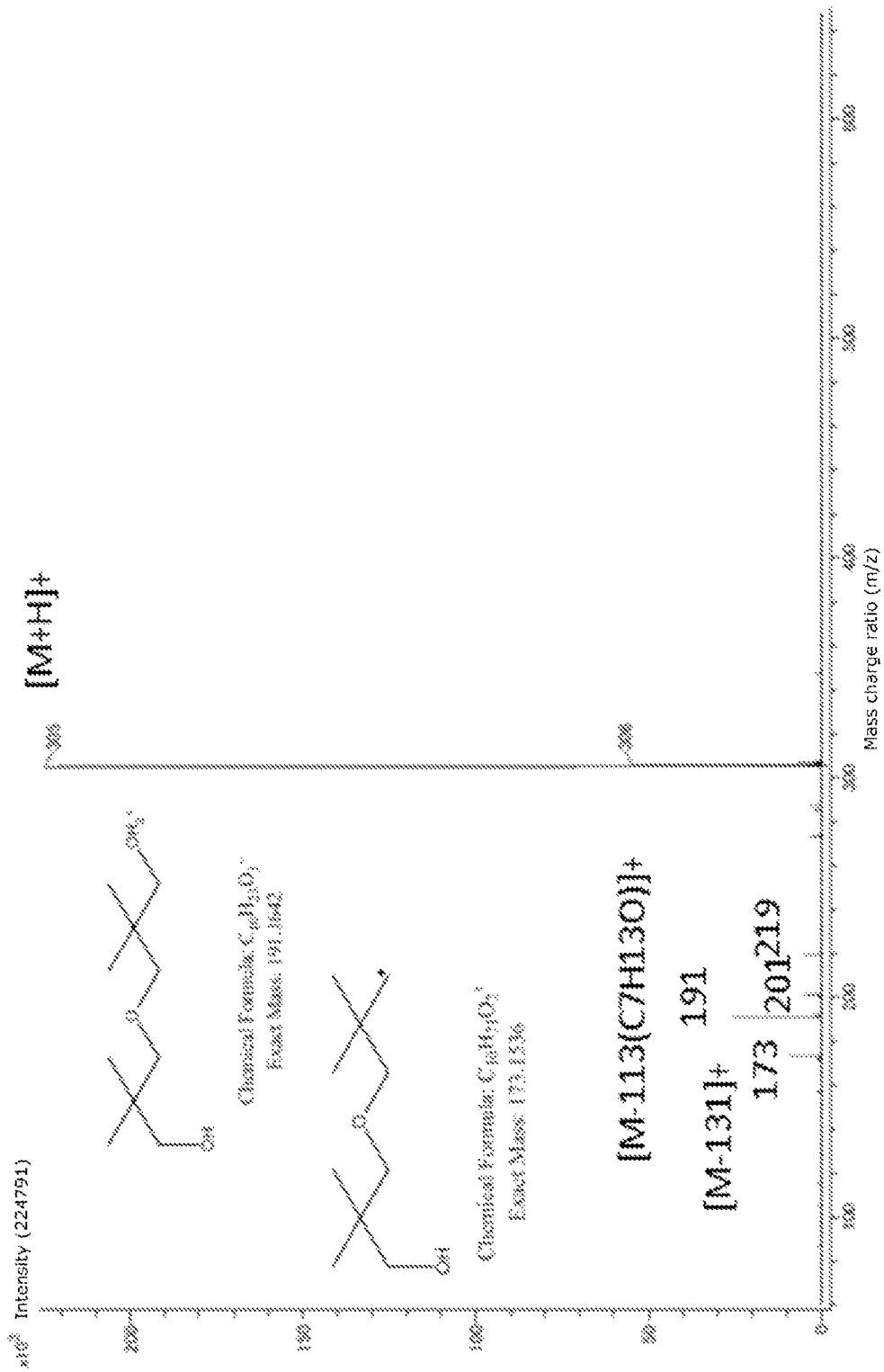
FIG. 2 is an MS spectrum of a compound MMMMEE.

CI+ spectra of the compound MMEEMM and the compound MMMMEE are respectively shown in FIGS. 1 and 2. Focusing attention on the fragmented portion, while the spectra of chemical species in which the 2,2-dimethyl-1,3-propanediol skeletons are connected by the ether bond are observed in the compound MMMMEE, the spectra are not observed in the compound MMEEMM. Therefore, the compound MMEEMM was identified as 3-[2-ethyl-2-(3-hydroxy-2,2-dimethyl-propoxymethyl)-butoxy]-2,2-dimethyl-propane-1-ol, and the compound MMMMEE was identified as 2-ethyl-2-[3-(3-hydroxy-2,2-dimethyl-propoxy)-2,2-dimethyl-propoxymethyl]-butane-1-ol.

The compound MMEEMM and the compound MMMMEE were isolated by chromatography, and the structures were confirmed also in NMR analysis. The results in NMR analysis were confirmed to agree with the structural analysis results derived from GC-MS analysis.

(Compound MMEEMM)
$^1$H NMR (500 MHz, CDCl$_3$) δ 0.80 (3H×2, 2t, C$\underline{H}_3$CH$_2$—×2), 0.89 (3H×4, s, Me$_2$C×4), 1.30 (2H×2, 2q, CH$_3$C$\underline{H}_2$C), 3.10-3.35 (8H, m, —CH$_2$—O—×4), 3.38-3.56 (6H, m —C$\underline{H}_2$OH×2 & OH×2); $^{13}$C NMR (125 MHz, CDCl$_3$) δ 7.24, 21.9, 23.6, 36.2, 41.0, 71.5, 77.4, 80.1.

(Compound MMMMEE)
$^1$H NMR (500 MHz, CDCl$_3$) δ 0.80 (3H×2, 2t, C$\underline{H}_3$CH$_2$—×2), 0.88, 0.89 (3H×4, 2s, Me$_2$C×4), 1.30 (2H×2, 2q, CH$_3$C$\underline{H}_2$C), 3.10-3.35 (8H, m, —CH$_2$—O—×4), 3.38-3.56 (6H, m, —C$\underline{H}_2$OH×2 & OH×2); $^{13}$C NMR (125 MHz, CDCl$_3$) δ 7.24, 21.8, 22.4, 22.7 35.9, 36.3, 40.9, 68.4, 71.3, 74.0, 77.3, 77.4, 79.9.

(Compound MMEEMM)

(Compound MMMMEE)

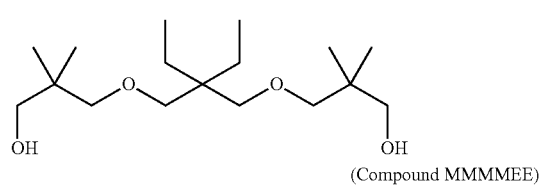

Similarly, it is found that the compound MMEEEE and the compound EEMMEE have a composition formula $C_{19}H_{40}O_4$, and have a 2,2-dimethyl-1,3-propanediol skeleton and two 2,2-diethyl-1,3-propanediol skeletons in the molecule; and these are connected by the ether bond. The compound MMEEEE and the compound EEMMEE are considered to be isomers in which the arrangement of substituted 1,3-propanediol skeletons is different.

Figure 3:
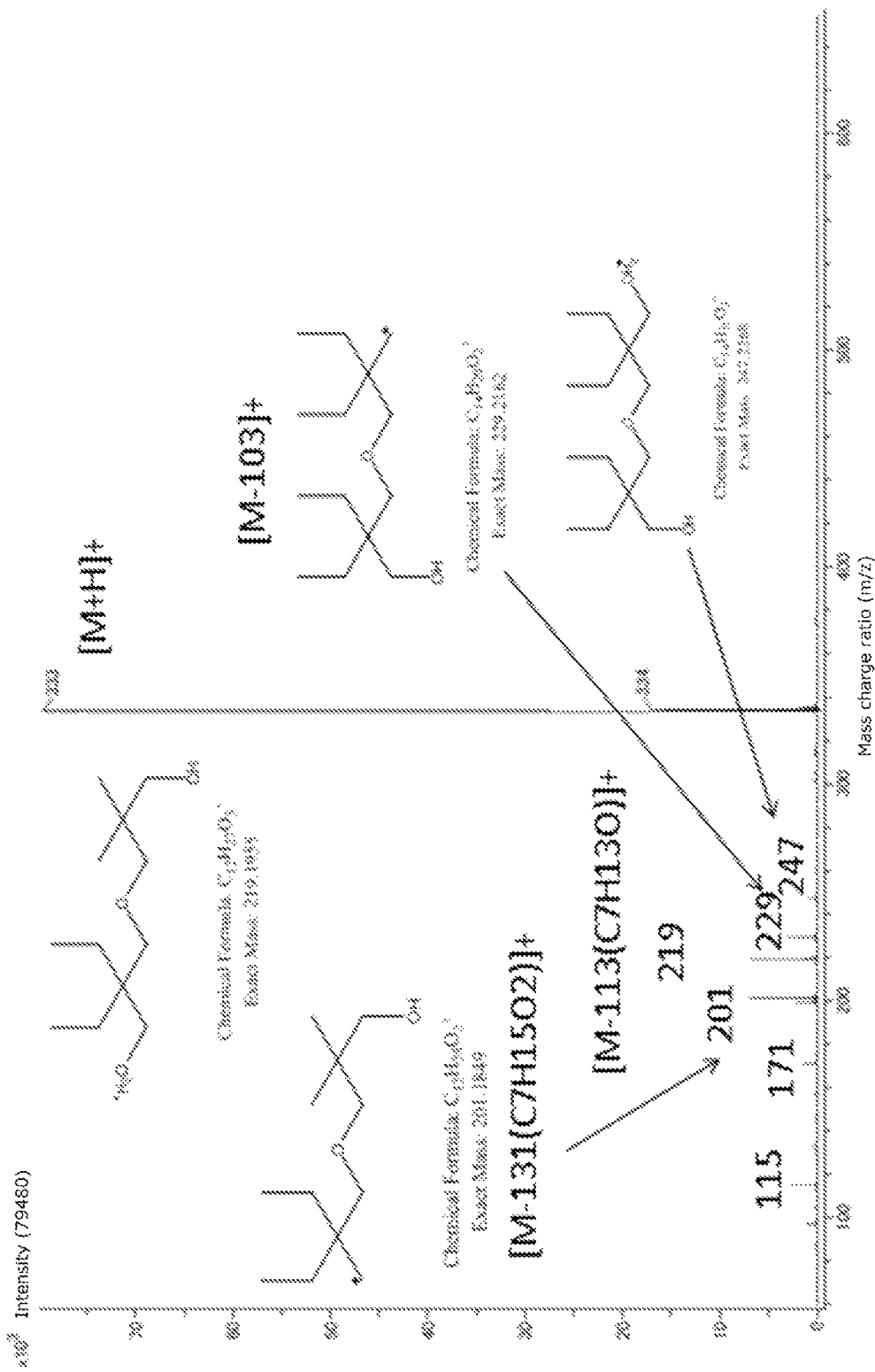
FIG. 3 is an MS spectrum of a compound MMEEEE.
Figure 4:
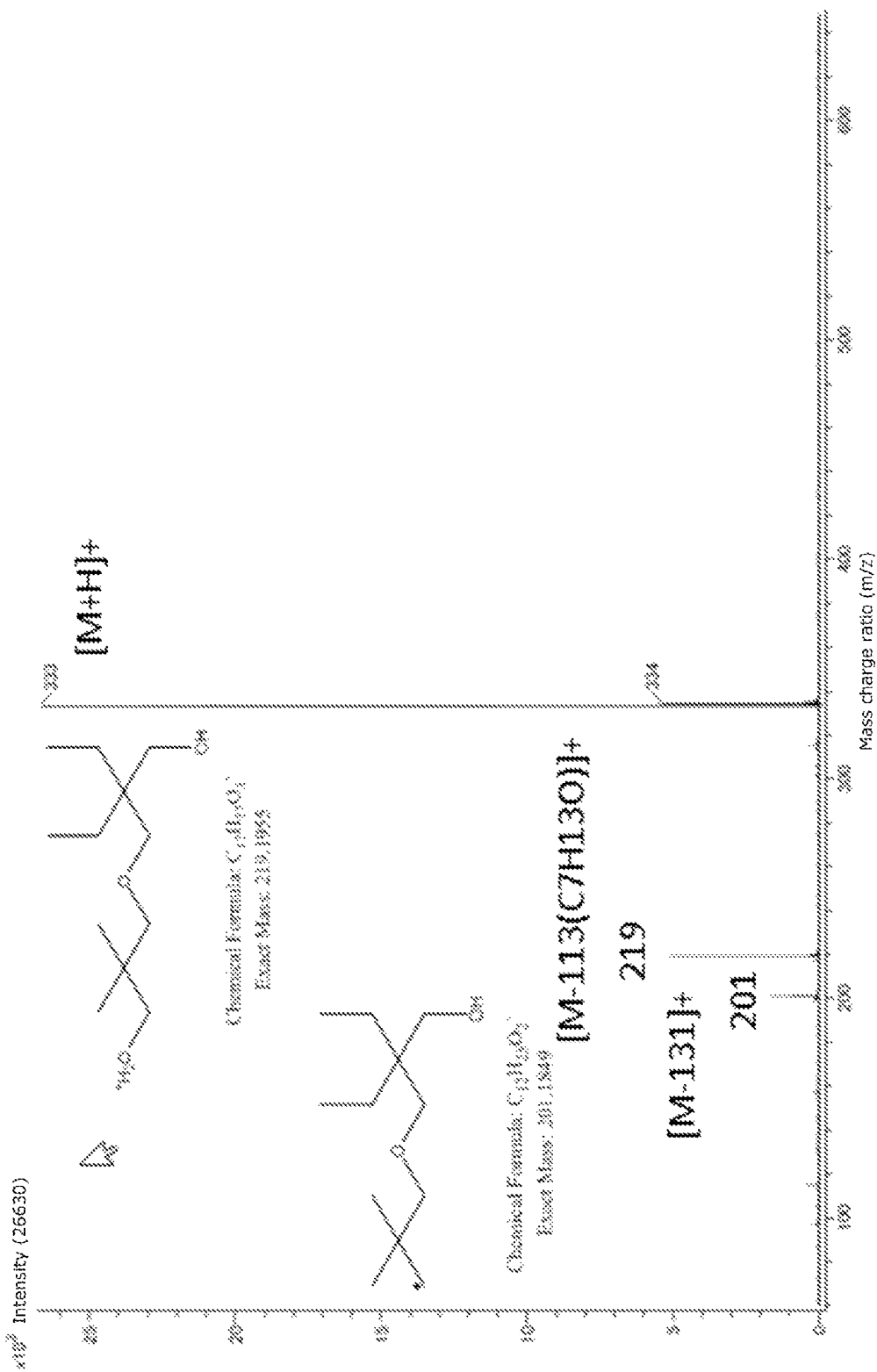
FIG. 4 is an MS spectrum of a compound EEMMEE.

CI+ spectra of the compound MMEEEE and the compound EEMMEE are respectively shown in FIGS. 3 and 4. Focusing attention on the fragmented portion, while the spectra of chemical species in which the 2,2-diethyl-1,3-propanediol skeletons are connected by the ether bond are observed in the compound MMEEEE, the spectra are not observed in the compound EEMMEE. Therefore, the compound MMEEEE was identified as 2-ethyl-2-[2-ethyl-2-(3-hydroxy-2,2-dimethyl-propoxymethyl)-butoxymethyl]-butane-1-ol, and the compound EEMMEE was identified as 2-ethyl-2-[3-(2-ethyl-2-hydroxymethyl-butoxy)-2,2-dimethyl-propoxymethyl]-butane-1-ol.

(Compound MMEEEE)

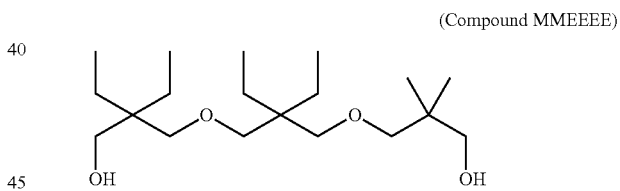

(Compound EEMMEE)

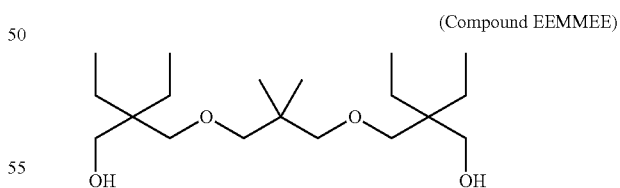

When the compound (1) was subjected to hydrogenation reduction as in Example 1, a polyether diol (compound (2)) having a ring-opening structure formed by adding one hydrogen molecule was generated, and the compound (3) in which a neo skeleton included in the compound (2) generated herein was further added to the compound (2) was also confirmed to be simultaneously generated also in Example 7. The reaction scheme will be shown below.

Reaction of Example 7

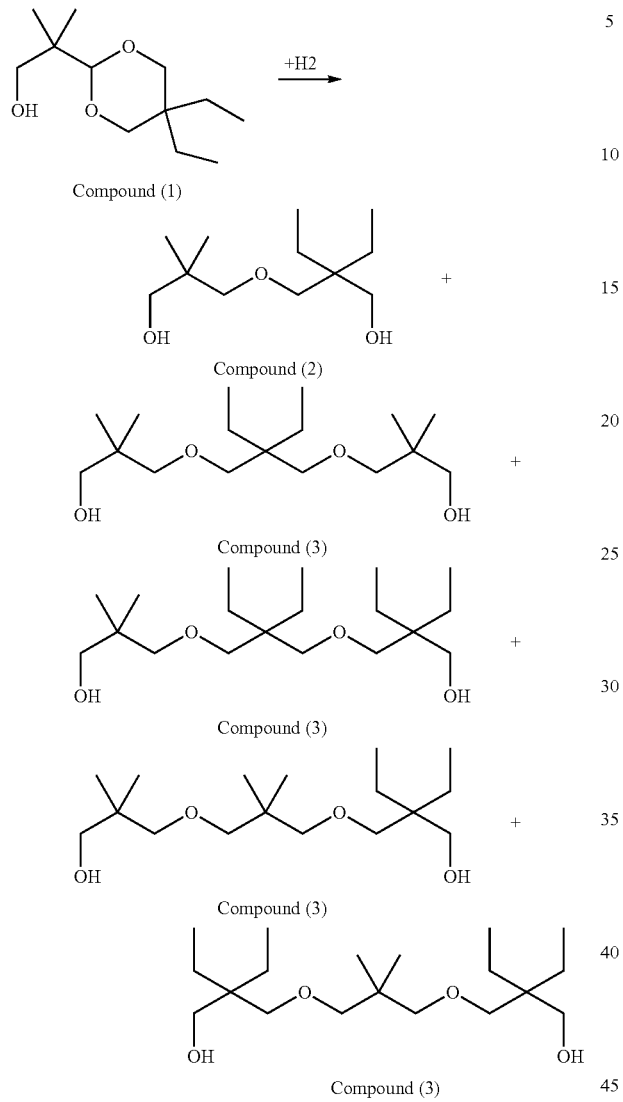

In Examples 8 and 9, 2-ethyl-2-(3-hydroxy-2,2-dimethyl-propoxymethyl)-hexane-1-ol (hereinafter, represented as "MMEB") was generated as the compound (2). 3-[2-Ethyl-2-(3-hydroxy-2,2-dimethyl-propoxymethyl)-hexyloxy]-2,2-dimethyl-propane-1-ol (hereinafter, represented as "MMEBMM) and 2-ethyl-2-[3-(3-hydroxy-2,2-dimethyl-propoxy)-2,2-dimethyl-propoxymethyl]-hexane-1-ol (hereinafter, represented as "MMMMEB") were mainly generated as a compound (3).

The product materials were identified by the following method.

(Compound MMEB)

The obtained reaction liquid was filtered to separate the catalyst. Then, the reaction liquid was isolated by distillation to obtain a product material. The structure of the product material was confirmed by subjecting the product material to NMR analysis.

$^1$H NMR (500 MHz, CDCl$_3$) δ 0.81 (3H, t, C$\underline{H}_3$CH$_2$CH$_2$—), 0.90 (9H, m, Me$_2$C×2 & C$\underline{H}_3$CH$_2$C), 1.10-1.38 (8H, m, CH$_3$C$\underline{H}_2$CH$_2$CH$_2$— & CH$_3$C$\underline{H}_2$C), 2.60 (1H, bs, OH), 2.68 (1H, bs, OH) 3.24, 3.30 (2H×2, 2s, —CH$_2$—O—×2), 3.41, 3.47 (2H×2, 2s, —C$\underline{H}_2$OH×2); $^{13}$C NMR (125 MHz, CDCl$_3$) δ 7.3, 14.1, 21.8, 23.5, 23.6, 25.0, 30.4, 36.4, 41.0, 67.9, 70.6, 79.4, 79.5.

The compound MMEB was a fluid at room temperature (20° C.). Therefore, it was found that the melting point of the compound MMEB is lower than the melting point (125° C.) of 2,2-dimethyl-1,3-propanediol and the melting point (42° C.) of 2-ethyl-2-butyl-1,3-propanediol. It was found that the melting point of the compound MMEB is lower than melting point (85° C.) of di-neopentyl glycol having a similar structure and having excellent symmetry.

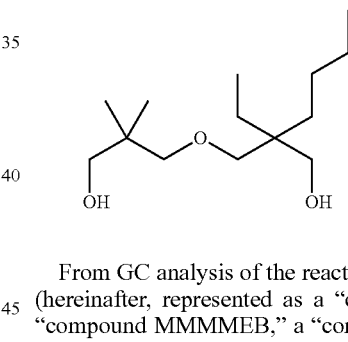

From GC analysis of the reaction liquid, four compounds (hereinafter, represented as a "compound MMEBMM," a "compound MMMMEB," a "compound MMEBEB," and a "compound EBMMEB") were confirmed to be generated. These analyses were performed by the same technique as that of Example 7, and the results shown in Table 4 were obtained.

TABLE 4

| | Actual measurement value (mu) | Estimated composition formula | Calculated mass (mu) | Mass difference (mu) | |
|---|---|---|---|---|---|
| Compound MMEBMM | 333.30248 | $^{12}$C$_{19}$$^1$H$_{41}$$^{16}$O$_4$ | 333.30048 | 0.00199 | [M + H]$^+$ |
| | 247.22665 | $^{12}$C$_{14}$$^1$H$_{31}$$^{16}$O$_3$ | 247.22732 | −0.00067 | [M − 85]$^+$ |
| | 229.21551 | $^{12}$C$_{14}$$^1$H$_{29}$$^{16}$O$_2$ | 229.21675 | −0.00124 | [M − 103]$^+$ |
| | 199.16880 | $^{12}$C$_{12}$$^1$H$_{23}$$^{16}$O$_2$ | 199.16980 | −0.00100 | |
| | 171.13759 | $^{12}$C$_{10}$$^1$H$_{19}$$^{16}$O$_2$ | 171.13850 | −0.00092 | |
| Compound MMMMEB | 333.30083 | $^{12}$C$_{19}$$^1$H$_{41}$$^{16}$O$_4$ | 333.30048 | 0.00035 | [M + H]$^+$ |
| | 191.16456 | $^{12}$C$_{10}$$^1$H$_{23}$$^{16}$O$_3$ | 191.16472 | −0.00160 | [M − 141]$^+$ |
| | 173.15409 | $^{12}$C$_{10}$$^1$H$_{21}$$^{16}$O$_2$ | 173.15415 | −0.00060 | [M − 159]$^+$ |
| Compound MMEBEB | 389.36189 | $^{12}$C$_{23}$$^1$H$_{49}$$^{16}$O$_4$ | 389.36308 | −0.00120 | [M + H]$^+$ |
| | 303.29055 | $^{12}$C$_{18}$$^1$H$_{39}$$^{16}$O$_3$ | 303.28992 | 0.00063 | [M − 85]$^+$ |
| | 285.27994 | $^{12}$C$_{18}$$^1$H$_{37}$$^{16}$O$_2$ | 285.27935 | 0.00058 | [M − 103]$^+$ |
| | 247.22701 | $^{12}$C$_{14}$$^1$H$_{31}$$^{16}$O$_3$ | 247.22732 | −0.00031 | [M − 141]$^+$ |

TABLE 4-continued

| | Actual measurement value (mu) | Estimated composition formula | Calculated mass (mu) | Mass difference (mu) | |
|---|---|---|---|---|---|
| | 229.21607 | $^{12}C_{14}{}^{1}H_{29}{}^{16}O_2$ | 229.21675 | −0.00069 | [M − 159]$^+$ |
| | 143.14289 | $^{12}C_9{}^{1}H_{19}{}^{16}O_1$ | 143.14359 | −0.00070 | |
| Compound EBMMEB | 389.36078 | $^{12}C_{23}{}^{1}H_{49}{}^{16}O_4$ | 389.36308 | −0.00231 | [M + H]$^+$ |
| | 247.22704 | $^{12}C_{14}{}^{1}H_{31}{}^{16}O_3$ | 247.22732 | −0.00028 | [M − 141]$^+$ |
| | 229.21599 | $^{12}C_{14}{}^{1}H_{29}{}^{16}O_2$ | 229.21675 | −0.00076 | [M − 159]$^+$ |
| | 143.14208 | $^{12}C_9{}^{1}H_{19}{}^{16}O_1$ | 143.14359 | −0.00151 | |

From the mass number (molecular weight M+1) of [M+H]$^+$ protonated while the molecular structure is held, it is found that the compound MMEBMM and the compound MMMMEB have a composition formula $C_{19}H_{40}O_4$, i.e., have two 2,2-dimethyl-1,3-propanediol skeletons and a 2-ethyl-2-butyl-1,3-propanediol skeleton in the molecule; and these are connected by the ether bond. The compound MMEBMM and the compound MMMMEB are considered to be isomers in which the arrangement of substituted 1,3-propanediol skeletons is different.

Figure 5:
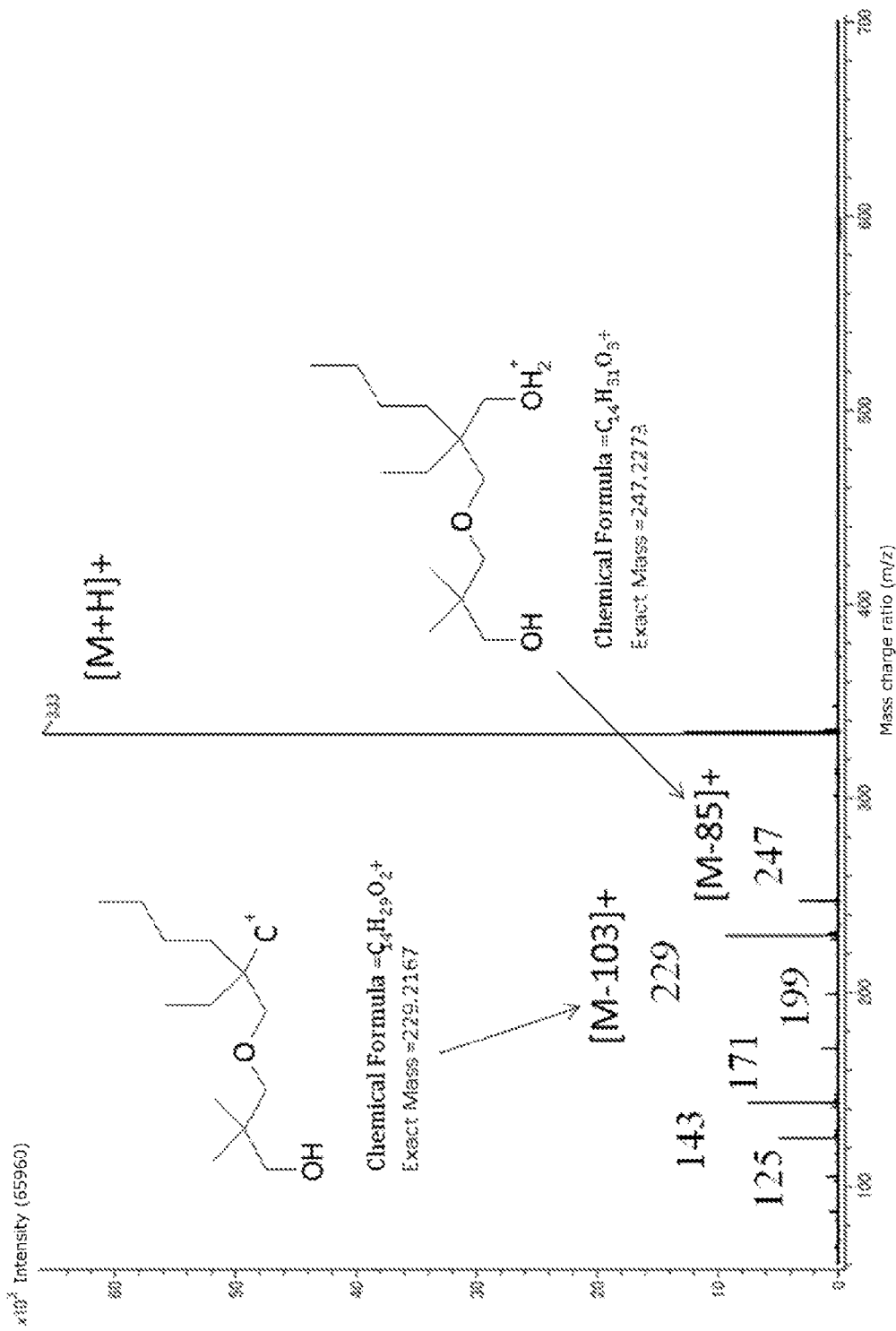
FIG. 5 is an MS spectrum of a compound MMEBMM.
Figure 6:
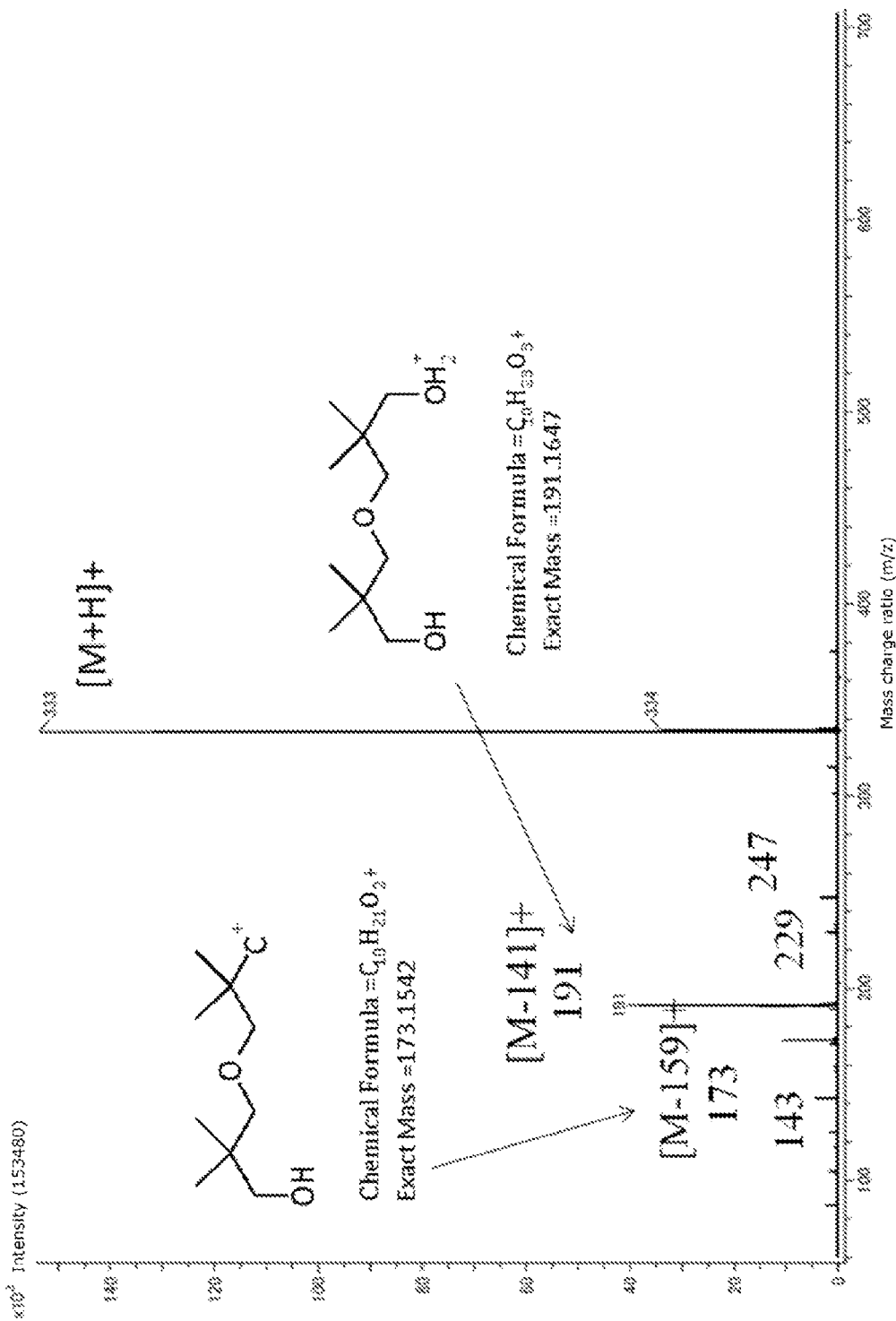
FIG. 6 is an MS spectrum of a compound MMMMEB.

Cl+ spectra of the compound MMEBMM and the compound MMMMEB are respectively shown in FIGS. 5 and 6. Focusing attention on the fragmented portion, while the spectra (mass numbers 173 and 191) of chemical species in which the 2,2-dimethyl-1,3-propanediol skeletons are connected by the ether bond are observed in the compound MMMMEB, the spectra are not observed in the compound MMEBMM. Therefore, the compound MMEBMM was identified as 3-[2-ethyl-2-(3-hydroxy-2,2-dimethyl-propoxymethyl)-hexyloxy]-2,2-dimethyl-propane-1-ol, and the compound MMMMEB was identified as 2-ethyl-2-[3-(3-hydroxy-2,2-dimethyl-propoxy)-2,2-dimethyl-propoxymethyl]-hexane-1-ol.

The compound MMEBMM and the compound MMMMEB were isolated by chromatography, and the structures were confirmed also in NMR analysis. The results in NMR analysis were confirmed to agree with the structural analysis results derived from GC-MS analysis.

(Compound MMEBMM)

$^1$H NMR (500 MHz, CDCl$_3$) δ 0.79 (3H, t, C$\underline{H}_3$CH$_2$CH$_2$—), 0.83-0.91 (15H, m, Me$_2$C×2 & C$\underline{H}_3$CH$_2$C), 1.10-1.39 (8H, m, CH$_3$C$\underline{H}_2$C$\underline{H}_2$C$\underline{H}_2$— & CH$_3$C$\underline{H}_2$C), 3.19, 3.22 (2H×4, 2s, —CH$_2$—O—×4), 3.41 (2H×2, s, —C$\underline{H}_2$OH×2) 3.51 (2H, bs, OH×2); $^{13}$C NMR (125 MHz, CDCl$_3$) δ7.50, 14.3, 22.1, 22.6, 23.7, 24.4, 25.1, 31.2, 36.4, 71.7, 74.5, 80.3.

(Compound MMMMEB)

$^1$H NMR (500 MHz, CDCl$_3$) δ 0.80 (3H, t, C$\underline{H}_3$CH$_2$CH$_2$—), 0.88-0.91 (15H, m, Me$_2$C×2 & C$\underline{H}_3$CH$_2$C), 1.10-1.38 (8H, m, CH$_3$C$\underline{H}_2$C$\underline{H}_2$C$\underline{H}_2$— & CH$_3$C$\underline{H}_2$C), 3.14, 3.15, 3.23, 3.28 (2H×4, 4s, —CH$_2$—O—×4), 3.40, 3.46 (2H×2, 2s, —C$\underline{H}_2$OH×2) 3.50 (2H, bs OH×2); $^{13}$C NMR (125 MHz, CDCl$_3$) δ 7.53, 14.3, 22.0, 22.6, 23.5, 23.8, 25.2, 30.4, 36.1, 36.5, 41.1, 69.0, 71.5, 77.6, 77.6, 77.8, 80.1.

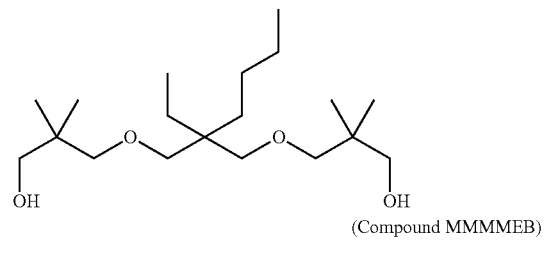

(Compound MMEBMM)

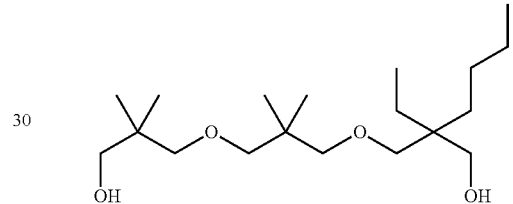

(Compound MMMMEB)

Similarly, it is found that the compound MMEBEB and the compound EBMMEB have a composition formula $C_{23}H_{48}O_4$, and have a 2,2-dimethyl-1,3-propanediol skeleton and two 2-ethyl-2-butyl-1,3-propanediol skeletons in the molecule; and these are connected by the ether bond. The compound MMEBEB and the compound EBMMEB are considered to be isomers in which the arrangement of substituted 1,3-propanediol skeletons is different.

Figure 7:
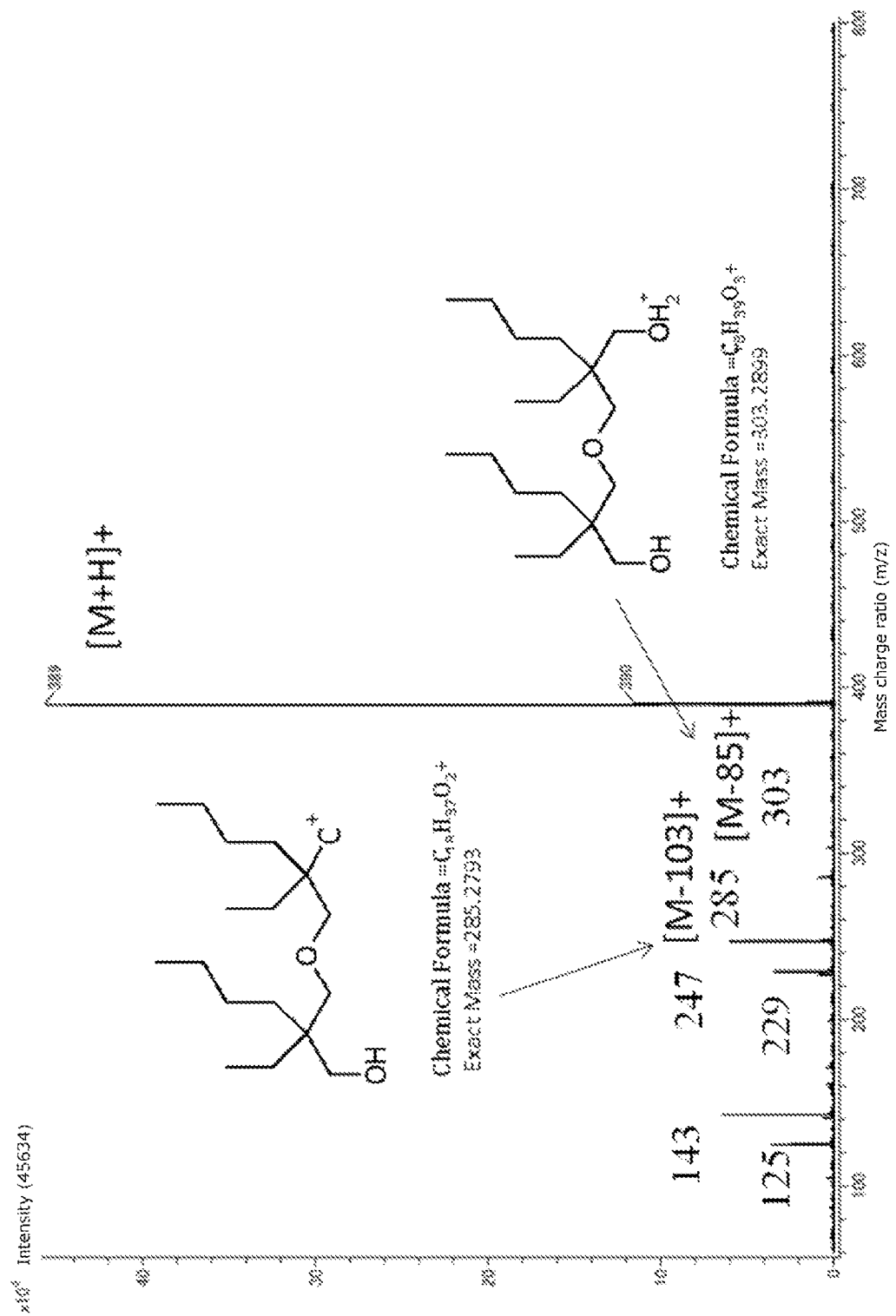
FIG. 7 is an MS spectrum of a compound MMEBEB.
Figure 8:
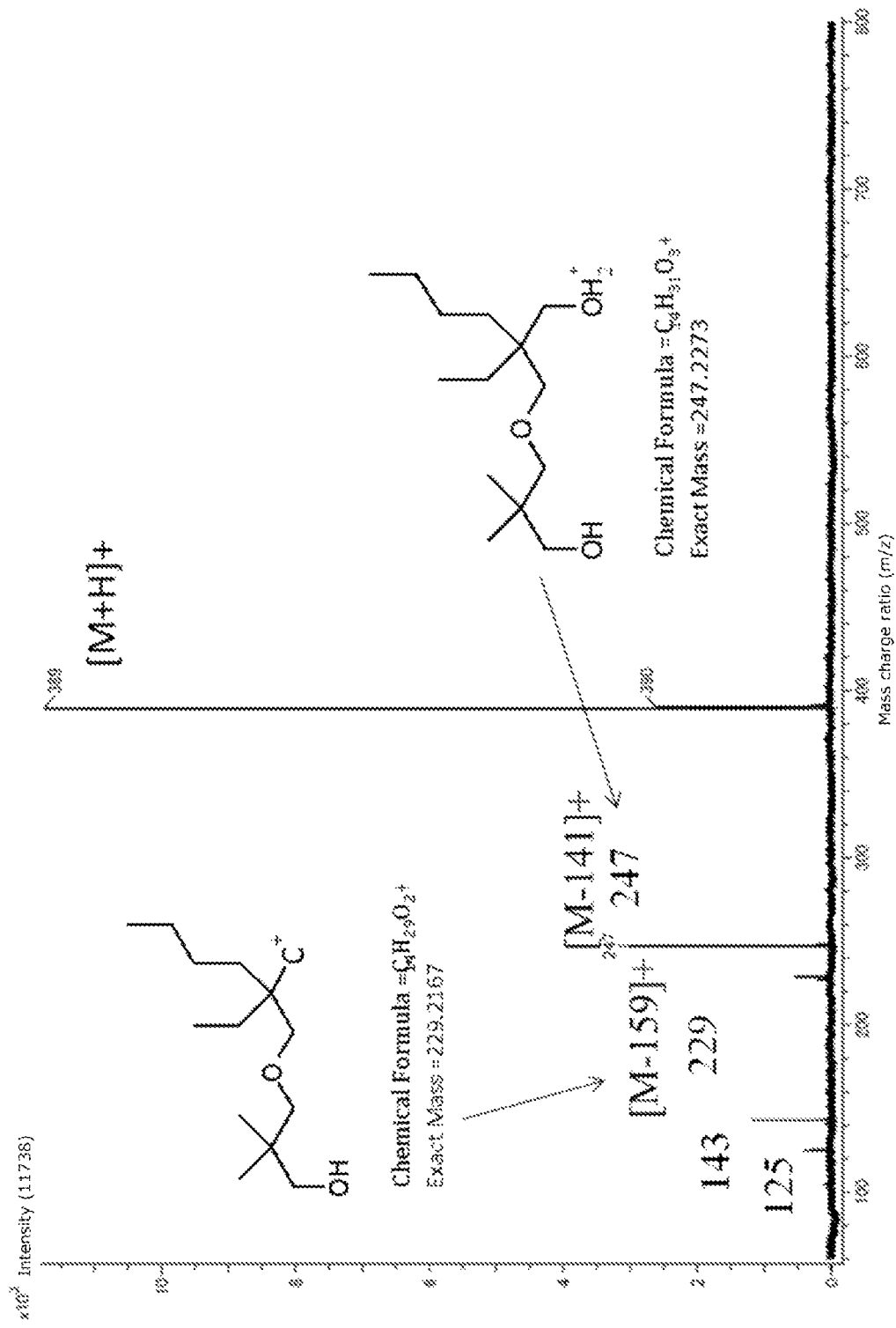
FIG. 8 is an MS spectrum of a compound EBMMEB.

Cl+ spectra of the compound MMEBEB and the compound EBMMEB are respectively shown in FIGS. 7 and 8. Focusing attention on the fragmented portion, while the spectra (mass numbers 285 and 303) of chemical species in which the 2-ethyl-2-butyl-1,3-propanediol skeletons are connected by the ether bond are observed in the compound MMEBEB, the spectra are not observed in the compound EBMMEB. Therefore, the compound MMEBEB was identified as 2-ethyl-2-[2-ethyl-2-(3-hydroxy-2,2-dimethyl-propoxymethyl)-hexyloxymethyl]-hexane-1-ol, and the compound EBMMEB was identified as 2-ethyl-2-[3-(2-ethyl-2-hydroxymethyl-hexyloxy)-2,2-dimethyl-propoxymethyl]-hexane-1-ol.

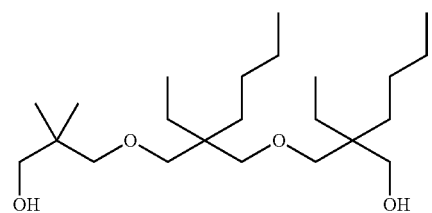

(Compound MMEBEB)

-continued (Compound EBMMEB)

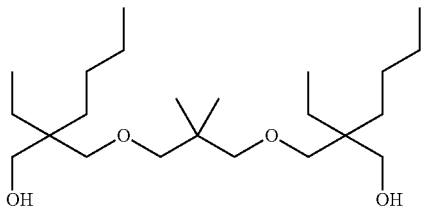

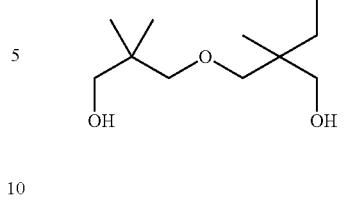

In Examples 10 and 11, 2-(3-hydroxy-2,2-dimethyl-propoxymethyl)-2-methyl-pentane-1-ol (hereinafter, represented as a "compound MMMP") was generated as the compound (2). 2-[3-(3-Hydroxy-2,2-dimethyl-propoxy)-2,2-dimethyl-propoxymethyl]-2-methyl-pentane-1-ol (hereinafter, represented as a "compound MMMMMP") and 3-[2-(3-hydroxy-2,2-dimethyl-propoxymethyl)-2-methyl-pentyloxy]-2,2-dimethyl-propane-1-ol (hereinafter, represented as a "compound MMMPMM") were mainly generated as the compound (3).

The product materials were identified by the following method.

(Compound MMMP)

The obtained reaction liquid was filtered to separate the catalyst. Then, the reaction liquid was isolated by distillation to obtain a product material. The structure of the product material was confirmed by subjecting the product material to NMR analysis.

$^1$H NMR (500 MHz, CDCl$_3$) δ 0.83 (3H, s, CH$_3$C), δ 0.91 (3H×3, 3s, Me$_2$C×2 & CH$_3$CH$_2$—), 1.20-1.38 (4H, m, CH$_3$CH$_2$CH$_2$—), 2.68-2.84 (2H, bs, OH×2), 3.21-3.30 (4H, m, —CH$_2$—O—×2), 3.41-3.45 (4H, m, —CH$_2$OH×2); $^{13}$C NMR (125 MHz, CDCl$_3$) δ 15.0, 16.5, 19.0, 21.8, 36.4, 37.0, 38.9, 69.7, 70.6, 78.4, 79.5.

The melting point of the compound MMMP obtained by differential thermal analysis was 35° C. This is lower than the melting point (125° C.) of 2,2-dimethyl-1,3-propanediol and the melting point (57° C.) of 2-propyl-2-methyl-1,3-propanediol. This is lower than the melting point (85° C.) of di-neopentyl glycol having a similar structure and excellent symmetry.

From GC analysis of the reaction liquid, three compounds (hereinafter, represented as a "compound MMMPMM," a "compound MMMMMP," and a "compound MMMPMP") were confirmed to be generated. These were analyzed by the same technique as that of Example 7, and the results shown in Table 5 were obtained.

TABLE 5

| | Actual measurement value (mu) | Estimated composition formula | Calculated mass (mu) | Mass difference (mu) | |
|---|---|---|---|---|---|
| Compound MMMPMM | 305.26985 | $^{12}C_{17}{}^{1}H_{37}{}^{16}O_4$ | 305.26918 | 0.00066 | [M + H]$^+$ |
| | 219.19581 | $^{12}C_{12}{}^{1}H_{27}{}^{16}O_3$ | 219.19602 | −0.00021 | [M − 85]$^+$ |
| | 201.18516 | $^{12}C_{12}{}^{1}H_{25}{}^{16}O_2$ | 201.18545 | −0.00029 | [M − 103]$^+$ |
| | 157.12296 | $^{12}C_9{}^{1}H_{17}{}^{16}O_2$ | 157.12285 | −0.00010 | |
| | 115.11205 | $^{12}C_7{}^{1}H_{15}{}^{16}O_1$ | 115.11229 | −0.00024 | |
| Compound MMMMMP | 305.27101 | $^{12}C_{17}{}^{1}H_{37}{}^{16}O_4$ | 305.26918 | 0.00183 | [M + H]$^+$ |
| | 219.19565 | $^{12}C_{12}{}^{1}H_{27}{}^{16}O_3$ | 219.19602 | −0.00037 | [M − 85]$^+$ |
| | 201.18525 | $^{12}C_{12}{}^{1}H_{25}{}^{16}O_2$ | 201.18545 | −0.00021 | [M − 103]$^+$ |
| | 191.16430 | $^{12}C_{10}{}^{1}H_{23}{}^{16}O_3$ | 191.16472 | −0.00042 | [M − 113]$^+$ |
| | 173.15374 | $^{12}C_{10}{}^{1}H_{21}{}^{16}O_2$ | 173.15415 | −0.00042 | [M − 131]$^+$ |
| | 115.11202 | $^{12}C_7{}^{1}H_{15}{}^{16}O_1$ | 115.11229 | −0.00027 | |
| Compound MMMPMP | 333.29926 | $^{12}C_{19}{}^{1}H_{41}{}^{16}O_4$ | 333.30048 | −0.00122 | [M + H]$^+$ |
| | 247.22609 | $^{12}C_{14}{}^{1}H_{31}{}^{16}O_3$ | 247.22732 | −0.00123 | [M − 85]$^+$ |
| | 229.21622 | $^{12}C_{14}{}^{1}H_{29}{}^{16}O_2$ | 229.21675 | −0.00053 | [M − 103]$^+$ |
| | 201.18607 | $^{12}C_{12}{}^{1}H_{25}{}^{16}O_2$ | 201.18545 | 0.00062 | [M − 131]$^+$ |
| | 115.11236 | $^{12}C_7{}^{1}H_{15}{}^{16}O_1$ | 115.11229 | 0.00007 | |

From the mass number (molecular weight M+1) of [M+H]$^+$ protonated while the molecular structure is held, the compound MMMPMM and the compound MMMMMP have a composition formula C$_{17}$H$_{36}$O$_4$, i.e., have two 2,2-dimethyl-1,3-propanediol skeletons and a 2-propyl-2-methyl-1,3-propanediol skeleton in the molecule; and these are connected by the ether bond. The compound MMMPMM and the compound MMMMMP are considered to be isomers in which the arrangement of substituted 1,3-propanediol skeletons is different.

Figure 9:
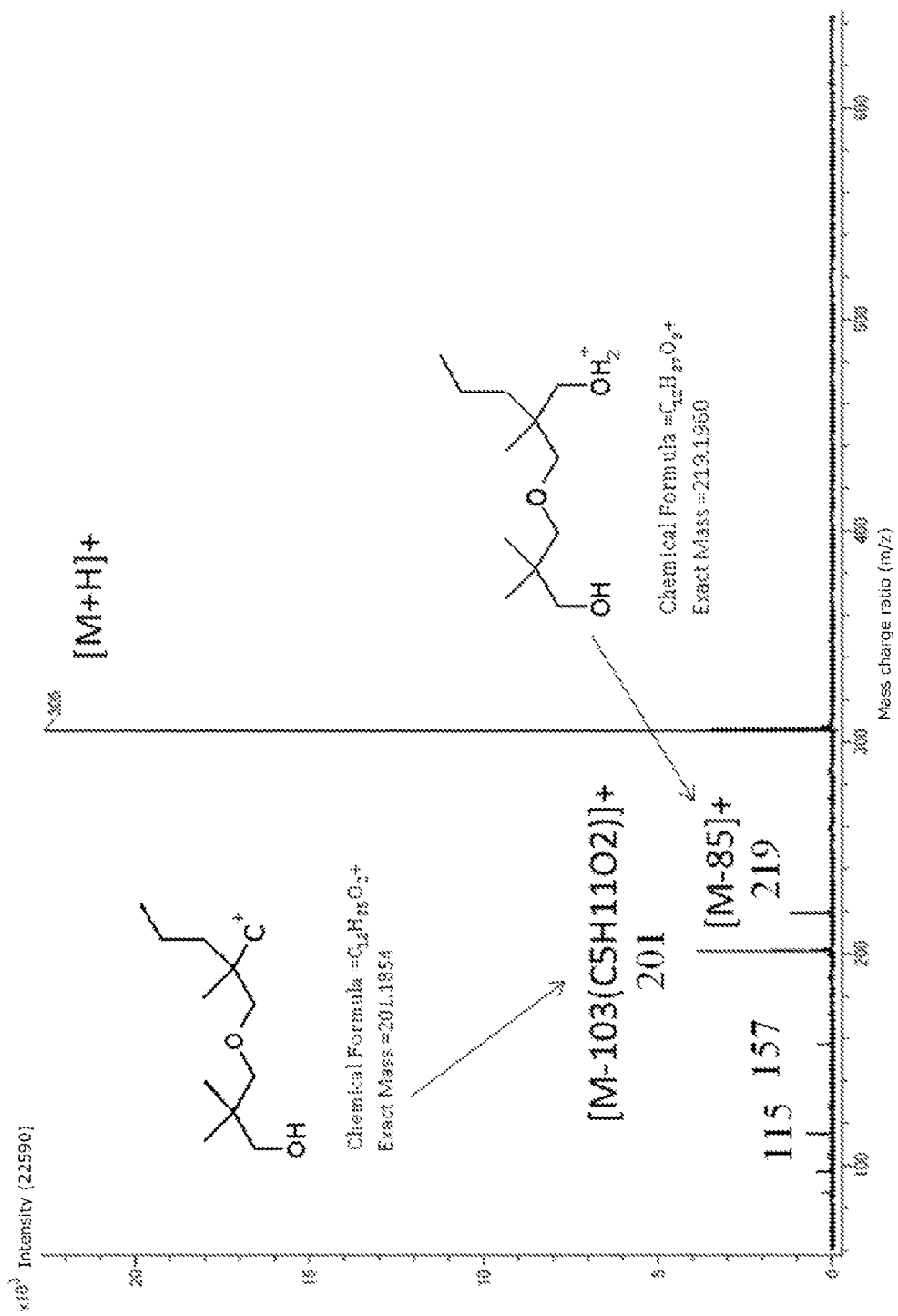
FIG. 9 is an MS spectrum of a compound MMMPMM.
Figure 10:
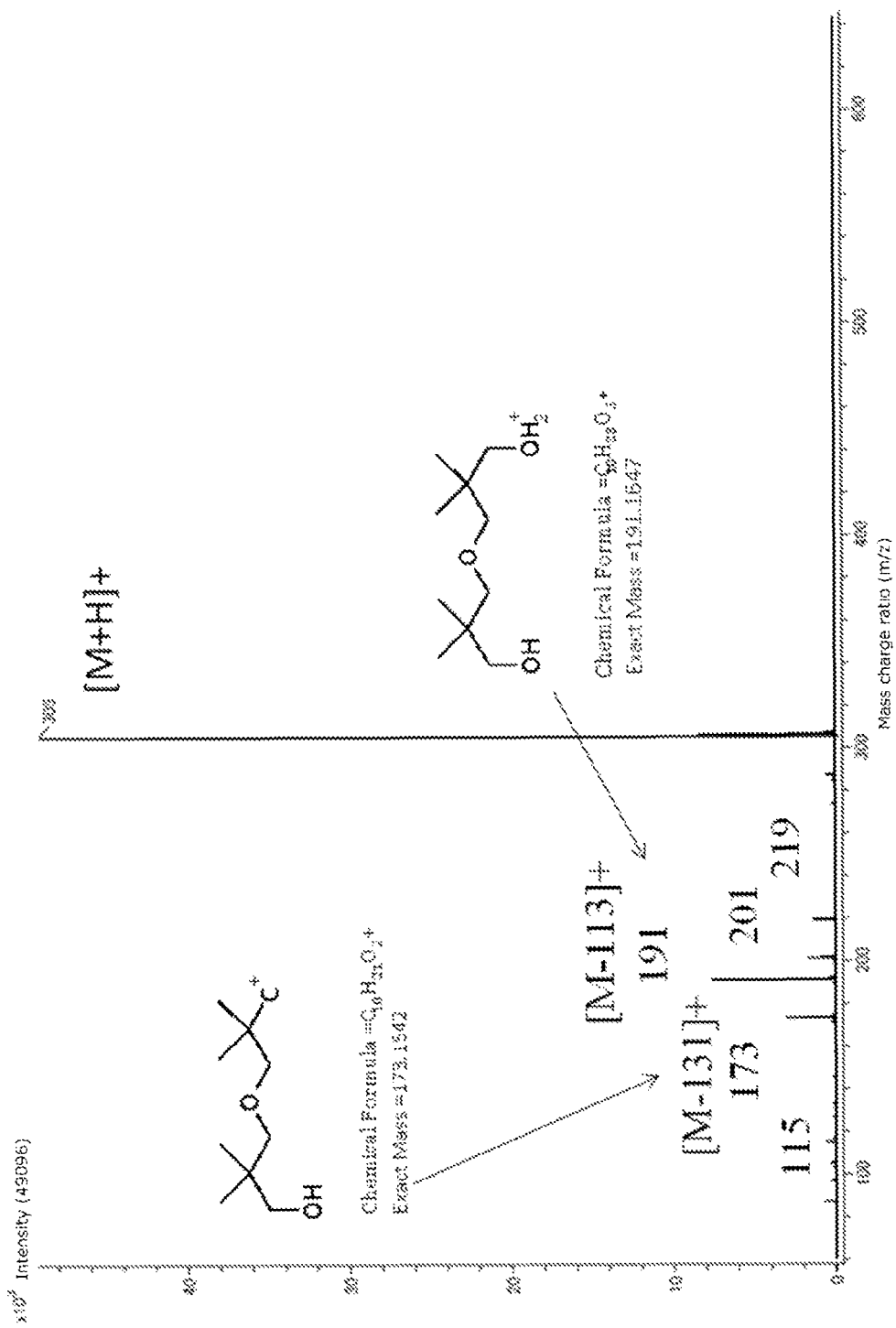
FIG. 10 is an MS spectrum of a compound MMMMMP.

CI+ spectra of the compound MMMPMM and the compound MMMMMP are respectively shown in FIGS. 9 and 10. Focusing attention on the fragmented portion, while the spectra (mass numbers 173 and 191) of chemical species in which the 2,2-dimethyl-1,3-propanediol skeletons are connected by the ether bond are observed in the compound MMMMMP, the spectra are not observed in the compound MMMPMM. Therefore, the compound MMMPMM was identified as 3-[2-(3-hydroxy-2,2-dimethyl-propoxymethyl)-2-methyl-pentyloxy]-2,2-dimethyl-propane-1-ol, and the compound MMMMMP was identified as 2-[3-(3-hydroxy-2,2-dimethyl-propoxy)-2,2-dimethyl-propoxymethyl]-2-methyl-pentane-1-ol.

The compound MMMPMM and the compound MMMMMP were isolated by chromatography, and the structures were confirmed also in NMR analysis. The results in NMR analysis were confirmed to agree with the structural analysis results derived from GC-MS analysis.

(Compound MMMPMM)

$^1$H NMR (500 MHz, CDCl$_3$) 0.83 (3H, s, C$\underline{H_3}$C), δ 0.85-0.93 (3H×5, m, Me$_2$C×2 & C$\underline{H_3}$CH$_2$—), 1.20-1.38 (4H, m, CH$_3$C$\underline{H_2}$CH$_2$—), 3.10-3.35 (8H, m, —CH$_2$—O—×4), 3.38-3.56 (6H, m, —C$\underline{H_2}$OH×2 & OH×2); $^{13}$C NMR (125 MHz, CDCl$_3$) δ 15.2, 16.6, 19.9, 22.6, 36.4, 37.9, 38.8, 71.7, 77.6, 80.3.

(Compound MMMMMP)

$^1$H NMR (500 MHz, CDCl$_3$) 0.81 (3H, s, C$\underline{H_3}$C), δ 0.85-0.93 (3H×5, m, Me$_2$C×2 & C$\underline{H_3}$CH$_2$—), 1.20-1.38 (4H, m, CH$_3$C$\underline{H_2}$CH$_2$—), 3.10-3.35 (8H, m, —CH$_2$—O—×4), 3.38-3.56 (6H, m, —C$\underline{H_2}$OH×2 & OH×2); $^{13}$C NMR (125 MHz, CDCl$_3$) δ 15.2, 16.7, 19.1, 22.0, 22.6, 36.2, 36.5, 37.1, 39.0, 70.7, 71.5, 76.4, 77.6, 79.2, 80.2.

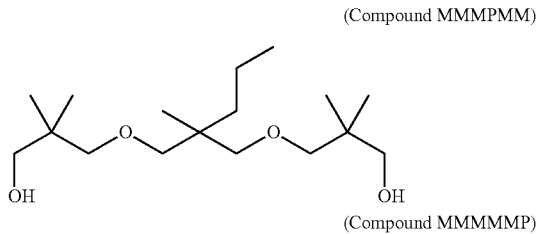

(Compound MMMPMM)

(Compound MMMMMP)

It is considered that the compound MMMPMP has a composition formula C$_{19}$H$_{40}$O$_4$, i.e., has a 2,2-dimethyl-1,3-propanediol skeleton and two 2-propyl-2-methyl-1,3-propanediol skeletons in the molecule; and these are connected by the ether bond.

Figure 11:
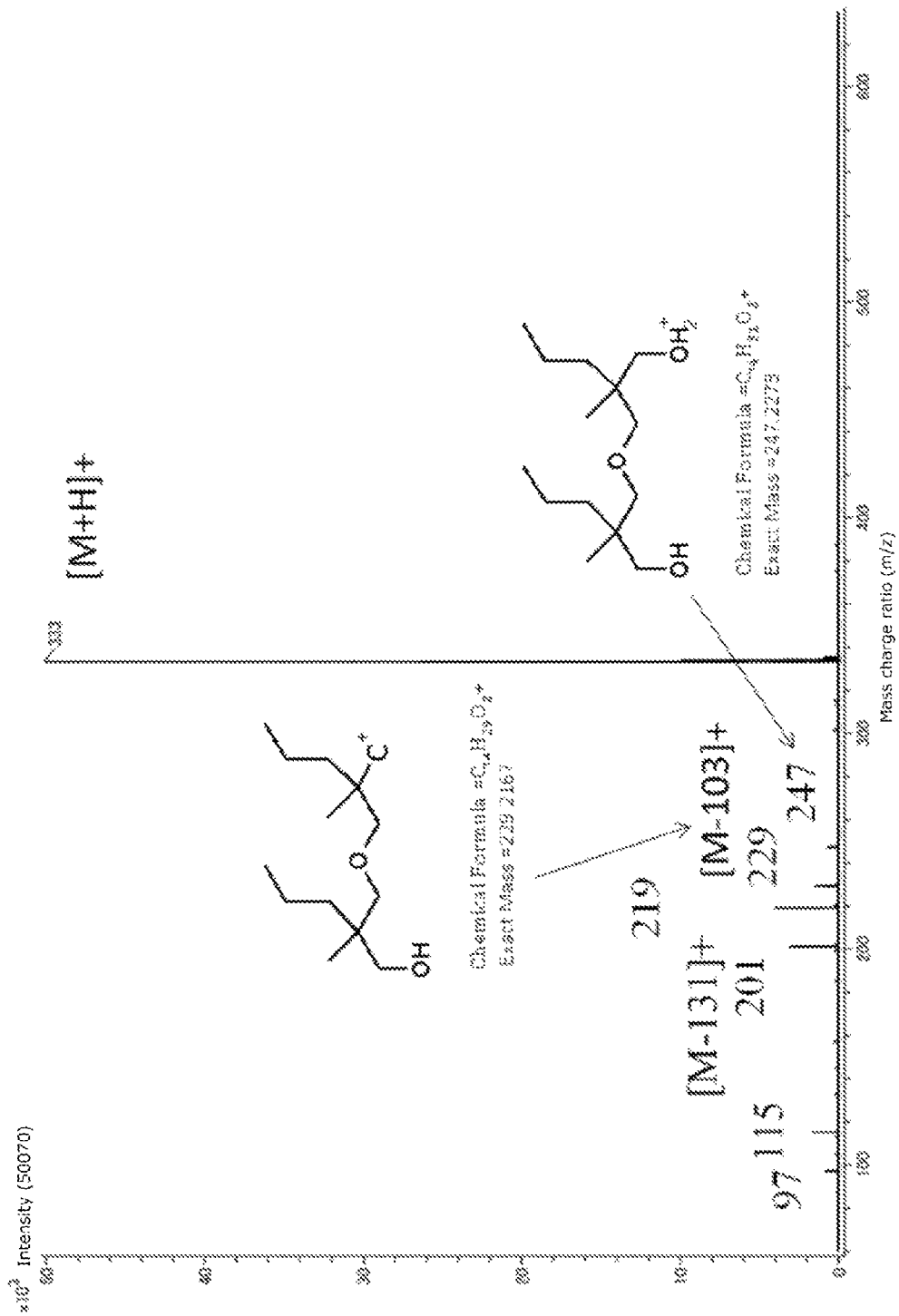
FIG. 11 is an MS spectrum of a compound MMMPMP.

CI+ spectrum of the compound MMMPMP is shown in FIG. 11. Focusing attention on the fragmented portion, while the spectra (mass numbers 229 and 247) of chemical species in which the 2-propyl-2-methyl-1,3-propanediol skeletons are connected by the ether bond are observed, the spectra (mass numbers 201 and 219) of the chemical species in which the 2-propyl-2-methyl-1,3-propanediol skeleton and the 2,2-dimethyl-1,3-propanediol skeleton are connected by the ether bond are also observed. Therefore, the compound MMMPMP was identified as 2-[2-(3-hydroxy-2,2-dimethyl-propoxymethyl)-2-methyl-pentyloxymethyl]-2-methyl-pentane-1-ol.

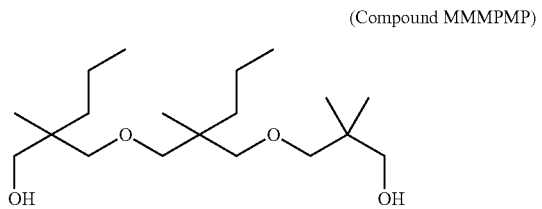 [SMILES: CCCC(C)(CO)COCC(C)(CCC)COCC(C)(C)CO]

(Compound MMMPMP)

Examples 12 to 15

Reactions were performed in the same manner as in Example 1 except that a B1 catalyst, a B2 catalyst, and a commercially available 5% by mass palladium-supported alumina catalyst (manufactured by Wako Pure Chemical Industries, Ltd., hereinafter, represented as a "B3 catalyst") were used as a hydrogenation catalyst, and a reaction temperature and a reaction time were changed. Kinds of the catalysts, reaction conditions, and reaction results are shown in Table 6.

TABLE 6

|  | Example 12 | Example 13 | Example 14 | Example 15 |
| --- | --- | --- | --- | --- |
| Catalyst name | B1 catalyst | B2 catalyst | B3 catalyst | B3 catalyst |
| Reaction temperature | 230° C. | 230° C. | 230° C. | 250° C. |
| Reaction time | 3.5 hr | 2.5 hr | 3.5 hr | 3.5 hr |
| Conversion of compound (1) | 74.9% | 75.8% | 92.8% | 98.3% |
| Selectivity of compound (2) | 90.3% | 92.4% | 82.9% | 66.6% |
| Selectivity of compound (3) | 2.9% | 3.2% | 5.8% | 14.0% |
| Selectivity of compounds (2) + (3) | 93.2% | 95.6% | 88.7% | 80.6% |

Example 16

A 100 mL SUS reactor vessel was purged with nitrogen gas. Then, 0.90 g of a Ni-1 catalyst, 2.40 g of 2-(5,5-dimethyl-[1,3]dioxane-2-yl)-2-methyl-propane-1-ol of raw material preparation example 1, and 24.0 g of diisopropyl-ether were placed. The reactor vessel was sealed, and then purged with nitrogen gas again. Then, the reactor vessel was filled with hydrogen gas at 8.5 MPa. The temperature was increased to a reaction temperature of 230° C. for the reaction for 5 hours. Then, the reactor vessel was cooled. The contents in the reactor vessel were sampled, and gas-chromatographically analyzed.

As a result, the conversion of a compound (1) was 61.0%. The selectivity of the compound MMMM of a compound (2) was 37.9%; the selectivity of the compound MMMMMM of a compound (3) was 7.6%; and the total of both the selectivities was 45.5%.

Examples 17 to 19

Reactions were performed in the same manner as in Example 16 except that kinds and amounts to be used of catalysts, reaction temperatures, and reaction times were changed. The kinds and amounts to be used of the catalysts, reaction conditions, and reaction results are shown in Table 7.

TABLE 7

|  | Example 16 | Example 17 | Example 18 | Example 19 |
| --- | --- | --- | --- | --- |
| Catalyst name | Ni-1 catalyst 0.90 g | Ni-1 catalyst 0.92 g | Cu-1 catalyst 2.00 g | Cu-1 catalyst 1.99 g |
| Reaction temperature | 230° C. | 210° C. | 230° C. | 210° C. |
| Reaction time | 5.0 hr | 5.0 hr | 5.0 hr | 5.0 hr |
| Conversion of compound (1) | 61.0% | 34.5% | 24.8% | 15.5% |
| Selectivity of compound (2) | 37.9% | 33.1% | 20.8% | 13.1% |
| Selectivity of compound (3) | 7.6% | 3.7% | 1.9% | 1.3% |

TABLE 7-continued

|  | Example 16 | Example 17 | Example 18 | Example 19 |
|---|---|---|---|---|
| Selectivity of compounds (2) + (3) | 45.5% | 36.8% | 22.7% | 14.4% |

Example 20

A tubular reactor (inner diameter: 10 mm, length: 300 mm) was filled with 4.1 g of an A3 catalyst. The temperature of the reactor was increased to 220° C. while a pressure in a reaction system was held at 8.0 MPa by hydrogen gas. From the top of the tubular reactor, a 10.0% by mass 2-(5,5-dimethyl-[1,3]dioxane-2-yl)-2-methyl-propane-1-ol/ diisopropylether solution was fed at a flow rate of 4.57 g/h while feeding hydrogen gas at a flow rate of 20 mL/min (in terms of normal condition), to perform hydrogenation reaction. The generated solution sampled from the lower outlet of the reactor was gas-chromatographically analyzed to evaluate the reaction results. As a result, the conversion of a compound (1) was 96.0%. The selectivity of a compound MMMM of a compound (2) was 81.0%; the selectivity of a compound MMMMMM of a compound (3) was 5.9%; and the total of both the selectivities was 86.9%.

Comparative Example 1

A reaction was performed in the same manner as in Example 1 except that 2.40 g of 2-(5,5-dimethyl-[1,3]dioxane-2-yl)-2-methyl-propane-1-ol of raw material preparation example 1 was changed to 2.36 g of 2-([1,3]dioxane-2-yl)-2-methyl-propane-1-ol of the reference raw material preparation example 1 as a reaction raw material. As a result, the conversion of a compound (1) was 100%. A very large number of decomposing materials mainly including a low-boiling component were by-produced, and only the trace amount of the subject matter was obtained.

Comparative Example 2

A reaction was performed in the same manner as in Comparative Example 1 except that a reaction temperature was changed to 210° C. and a reaction time was changed to 2 hours in reaction conditions. The result was the same as that of Comparative Example 1.

Comparative Example 3

A reaction was performed in the same manner as in Example 1 except that 2.40 g of 2-(5,5-dimethyl-[1,3]dioxane-2-yl)-2-methyl-propane-1-ol of raw material preparation example 1 was changed to 2.39 g of 2-(5-methyl-[1,3] dioxane-2-yl)-2-methyl-propane-1-ol of the reference raw material preparation example 2 as a reaction raw material. As a result, the conversion of a compound (1) was 99.1%. The selectivity of 3-(3-hydroxy-2-methyl-propoxy)-2,2-dimethyl-propane-1-ol of a compound (2) was 5.1%. The selectivity of a compound (3) was the trace amount. In addition to these, a very large number of decomposing materials mainly including a low-boiling component were observed to be by-produced. In the present Comparative Example, the reaction results were obtained by treating a 2-methyl-1,3-propanediol skeleton as in a neo skeleton. The reaction scheme of the reaction will be shown below.

Comparative Example 3

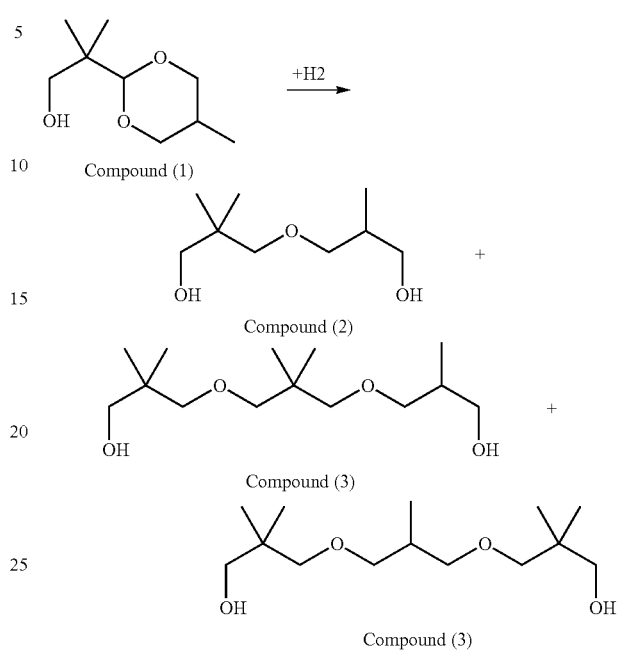

The producing method of the present invention subjects a compound (1) which is a cyclic acetal compound to hydrogenation reduction using a hydrogenation catalyst, and thereby a polyether diol can be efficiently produced. A novel polyether diol having a low melting point can be obtained.

The invention claimed is:

1. A method for producing a polyether diol, comprising subjecting a compound represented by the following general formula (1) to hydrogenation reduction in the presence of a hydrogenation catalyst to provide at least one polyether diol selected from the group consisting of compounds represented by the following general formulae (2), (3A), (3B), (3C), and (3D):

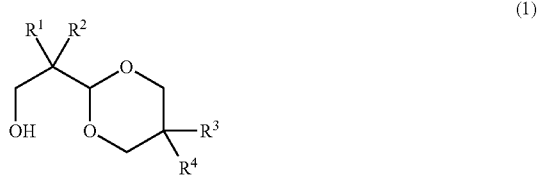

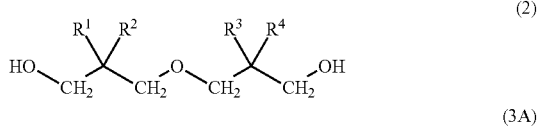

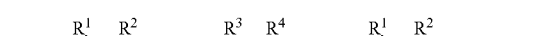

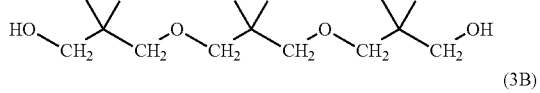

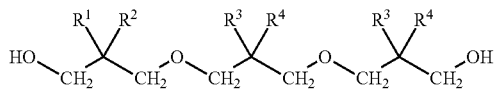

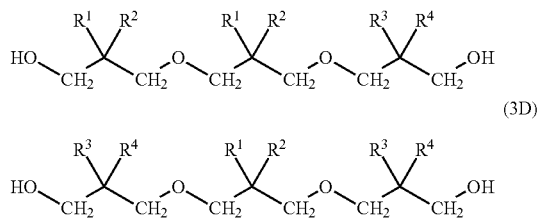

(3C)

(3D)

wherein in the formulae (1), (2), (3A), (3B), (3C), and (3D), $R^1$, $R^2$, $R^3$, and $R^4$ may be the same or different, and represent a linear or branched alkyl group having 1 to 6 carbon atoms; and in each of $R^1$, $R^2$, $R^3$, and $R^4$, independently, one or two or more hydrogen atoms contained in the alkyl group may be replaced with an alkoxy group having 6 or less carbon atoms or a functional group inactive for a hydrogenation reduction reaction.

2. The method according to claim 1, wherein the polyether diol is a compound represented by the general formula (2).

3. The method according to claim 1, wherein the polyether diol is at least one compound selected from the group consisting of the compounds represented by the general formulae (3A), (3B), (3C), and (3D).

4. The method according to claim 1, wherein the polyether diol is obtained with at least one polyether diol selected from the group consisting of by-produced polyether diols having 4 or more and 9 or less neo skeletons in a molecule.

5. The method according to claim 1, wherein at least a part of the compound represented by the general formula (1) is subjected to self-condensation, and thereafter hydrogenation reduction.

6. The method according to claim 1, wherein $R^1$ and $R^3$ are the same group, and $R^2$ and $R^4$ are the same group.

7. The method according to claim 1, wherein $R^1$ and $R^2$ are the same group, or $R^3$ and $R^4$ are the same group.

8. The method according to claim 1, wherein $R^1$ and $R^2$ are different groups, or $R^3$ and $R^4$ are different groups.

9. The method according to claim 1, wherein $R^1$, $R^2$, $R^3$, and $R^4$ are, in this order,
 a methyl group, a methyl group, a methyl group, and a methyl group;
 a methyl group, a methyl group, a methyl group, and an ethyl group;
 a methyl group, a methyl group, a methyl group, and a normal propyl group;
 a methyl group, a methyl group, a methyl group, and a normal butyl group;
 a methyl group, a methyl group, a methyl group, and a normal hexyl group;
 a methyl group, a methyl group, an ethyl group, and an ethyl group;
 a methyl group, a methyl group, an ethyl group, and a normal butyl group;
 a methyl group, a methyl group, a normal propyl group, and a normal pentyl group;
 a methyl group, an ethyl group, a methyl group, and an ethyl group;
 an ethyl group, an ethyl group, an ethyl group, and an ethyl group;
 a methyl group, a normal propyl group, a methyl group, and a normal propyl group;
 a methyl group, a normal butyl group, a methyl group, and a normal butyl group;
 a methyl group, a normal hexyl group, a methyl group, and a normal hexyl group;
 an ethyl group, a normal butyl group, an ethyl group, and a normal butyl group; or
 a normal propyl group, a normal pentyl group, a normal propyl group, and a normal pentyl group.

10. The method according to claim 1, wherein both $R^1$ and $R^2$ are methyl groups, or both $R^3$ and $R^4$ are methyl groups.

11. The method according to claim 1, wherein all of $R^1$, $R^2$, $R^3$, and $R^4$ are methyl groups.

12. The method according to claim 1, wherein the compound represented by the general formula (1) is subjected to hydrogenation reduction in a system containing an ether compound or a saturated hydrocarbon compound which is a reaction solvent.

13. The method according to claim 1, wherein the hydrogenation catalyst is a solid catalyst containing at least one selected from the group consisting of palladium, platinum, nickel, and copper.

14. The method according to claim 1, wherein the hydrogenation catalyst is a solid catalyst containing a zirconium compound or an apatite compound.

15. A polyether diol represented by the following general formula (A):

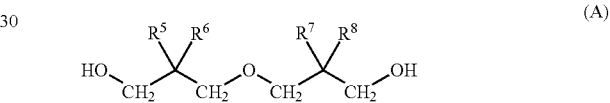

(A)

wherein in the formula (A), a combination of a group of $R^5$ and $R^6$ with a group of $R^7$ and $R^8$ is any one of (a1) to (a6) shown in the following table

| No. | $R^5$ and $R^6$ | $R^7$ and $R^8$ |
|---|---|---|
| a1 | $CH_3$ and $CH_3$ | $CH_3$ and $C_2H_5$ |
| a2 | $CH_3$ and $CH_3$ | $CH_3$ and $C_3H_7$ |
| a3 | $CH_3$ and $CH_3$ | $CH_3$ and $C_6H_{13}$ |
| a4 | $CH_3$ and $CH_3$ | $C_2H_5$ and $C_2H_5$ |
| a5 | $CH_3$ and $CH_3$ | $C_2H_5$ and $C_4H_9$ |
| a6 | $CH_3$ and $CH_3$ | $C_3H_7$ and $C_5H_{11}$. |

16. A polyether diol represented by the following general formula (B1) or (B2):

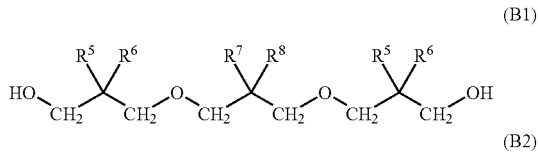

(B1)

(B2)

wherein in the formulae (B1) and (B2), $R^5$, $R^6$, $R^7$, and $R^8$ each independently represent a linear or branched alkyl group having 1 to 6 carbon atoms; in each of $R^5$, $R^6$, $R^7$, and $R^8$, independently, one or two or more hydrogen atoms contained in the alkyl group may be replaced with an alkoxy group having 6 or less carbon atoms or a functional group inactive for a hydrogenation reduction reaction; and at least one of $R^5$ and $R^6$ is a different group from at least one of $R^7$ and $R^8$.

17. The polyether diol according to claim 16, wherein $R^5$ and $R^6$ are different groups, or $R^7$ and $R^8$ are different groups.

18. The polyether diol according to claim 16, wherein both $R^5$ and $R^6$ are methyl groups, or both $R^7$ and $R^8$ are methyl groups.

* * * * *